United States Patent
James

(10) Patent No.: US 11,826,545 B2
(45) Date of Patent: Nov. 28, 2023

(54) OPTICAL BLOOD DETECTION SYSTEM

(71) Applicant: Fresenius Medical Care Holdings, Inc., Waltham, MA (US)

(72) Inventor: Philip Scott James, Orinda, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 459 days.

(21) Appl. No.: 15/259,754

(22) Filed: Sep. 8, 2016

(65) Prior Publication Data

US 2018/0064871 A1    Mar. 8, 2018

(51) Int. Cl.
*A61M 5/168*    (2006.01)
*A61M 1/36*    (2006.01)
(Continued)

(52) U.S. Cl.
CPC ....... *A61M 5/16836* (2013.01); *A61B 5/1455* (2013.01); *A61M 1/3656* (2014.02);
(Continued)

(58) Field of Classification Search
CPC ...... A61M 2205/3306; A61M 2205/15; A61B 5/02042
See application file for complete search history.

(56) References Cited

U.S. PATENT DOCUMENTS 4,017,190 A * 4/1977 Fischel ................. G01N 21/85
356/414
5,372,136 A    12/1994 Steuer et al.
(Continued)

FOREIGN PATENT DOCUMENTS

CN    101490855 A    7/2009
CN    101505812 A    8/2009
(Continued)

OTHER PUBLICATIONS

PCT International Search Report and Written Opinion in International Application No. PCT/US2017/050419, dated Nov. 29, 2017, 14 pages (with English translation).
(Continued)

*Primary Examiner* — Tse W Chen
*Assistant Examiner* — Michael A Catina
(74) *Attorney, Agent, or Firm* — Fish & Richardson P.C.

(57) ABSTRACT

The present invention relates to an optical blood detector system that rapidly detects the presence of blood due to a blood leak in a system. The blood detector system contains a reusable blood sensor that is able to accurately detect the presence of blood in, for example, an extracorporeal blood treatment system by optically sensing light from a sensing region and determining if the light came from a leaked blood. The blood sensor may be responsive to reflected light or light emitted from blood due to bio-fluorescence excited by a light source in the blood detector system. The blood detector system can be placed against absorbent material adjacent to an intravenous needle injection site and quickly detect any blood wicked into the absorbent material. The blood detector system can eliminate the need for medical personnel to continuously inspect numerous patients visually for potentially fatal blood leaks due to needle dislodgement.

27 Claims, 13 Drawing Sheets

(51) Int. Cl.
*A61B 5/1455* (2006.01)
*A61M 5/50* (2006.01)

(52) U.S. Cl.
CPC ....... *A61M 5/5086* (2013.01); *A61M 2205/15* (2013.01); *A61M 2205/18* (2013.01); *A61M 2205/3306* (2013.01); *A61M 2205/3313* (2013.01); *A61M 2205/3569* (2013.01); *A61M 2205/3592* (2013.01); *A61M 2205/581* (2013.01); *A61M 2205/582* (2013.01); *A61M 2205/583* (2013.01); *A61M 2209/088* (2013.01)

(56) References Cited

U.S. PATENT DOCUMENTS

| | | | |
|---|---|---|---|
| 6,531,708 B1 | 3/2003 | Malmstrom et al. | |
| 6,572,576 B2 | 6/2003 | Brugger et al. | |
| 6,750,468 B2 | 6/2004 | Malmstrom et al. | |
| 6,793,827 B1 | 9/2004 | Bosetto et al. | |
| 7,040,142 B2 | 5/2006 | Burbank | |
| 7,087,033 B2 | 8/2006 | Brugger et al. | |
| 7,327,273 B2 | 2/2008 | Tung et al. | |
| 7,420,658 B2 | 9/2008 | Petterson et al. | |
| 7,605,710 B2 | 10/2009 | Crnkovich et al. | |
| 7,749,184 B2 | 7/2010 | Cavalcanti et al. | |
| 7,938,792 B2 | 5/2011 | Roger et al. | |
| 7,998,115 B2 | 8/2011 | Bedingfield | |
| 8,083,677 B2 | 12/2011 | Rohde | |
| 8,192,388 B2 | 6/2012 | Hogard | |
| 8,360,977 B2 | 1/2013 | Marttila et al. | |
| 8,518,247 B2 | 8/2013 | Akita et al. | |
| 8,529,485 B2 | 9/2013 | Bock et al. | |
| 8,654,318 B2 | 2/2014 | Slepicka | |
| 8,708,950 B2 | 4/2014 | Scarpaci et al. | |
| 8,777,887 B2 | 7/2014 | Joensson et al. | |
| 8,834,720 B2 | 9/2014 | Ahrens | |
| 8,845,570 B2 | 9/2014 | Akonur et al. | |
| 8,911,367 B2 | 12/2014 | Brister et al. | |
| 8,920,355 B2 | 12/2014 | Roger et al. | |
| 8,920,356 B2 | 12/2014 | Shang et al. | |
| 8,926,544 B2 | 1/2015 | Hogard | |
| 8,953,162 B2 | 2/2015 | Scarpaci et al. | |
| 8,981,948 B2 | 3/2015 | Olde et al. | |
| 9,011,334 B2 | 4/2015 | Bouton | |
| 2007/0135717 A1* | 6/2007 | Uenishi | A61B 5/6815 600/509 |
| 2008/0041792 A1* | 2/2008 | Crnkovich | A61F 13/42 210/739 |
| 2008/0195021 A1 | 8/2008 | Roger et al. | |
| 2008/0195060 A1* | 8/2008 | Roger | A61M 1/3653 604/246 |
| 2009/0076350 A1* | 3/2009 | Bly | A61B 5/02405 600/301 |
| 2009/0082649 A1* | 3/2009 | Muller | A61M 1/3653 600/310 |
| 2009/0250630 A1 | 10/2009 | Van Der Zaag et al. | |
| 2009/0312650 A1* | 12/2009 | Maile | A61B 5/0215 600/486 |
| 2011/0245682 A1* | 10/2011 | Robinson | A61M 1/0025 600/473 |
| 2011/0306855 A1* | 12/2011 | Rabinovitz | A61B 5/4283 600/310 |
| 2013/0217979 A1* | 8/2013 | Blackadar | A61B 5/1123 600/301 |
| 2014/0046150 A1 | 2/2014 | Maierhofer et al. | |
| 2016/0158517 A1* | 6/2016 | Nebbia | A61B 5/02042 604/111 |
| 2017/0173253 A1* | 6/2017 | Funkhouser | A61M 1/3653 |

FOREIGN PATENT DOCUMENTS

| | | |
|---|---|---|
| CN | 102811751 A | 12/2012 |
| CN | 104363820 A | 2/2015 |
| EP | 1736185 | 12/2006 |
| EP | 2526982 A2 | 11/2012 |
| EP | 2526982 A3 | 1/2013 |

OTHER PUBLICATIONS

International Preliminary Report on Patentability in Application No. PCT/US2017/050419, dated Mar. 12, 2019, 7 pages.

IRPA Guidelines on Protection Against Non-Ionizing Radiation: The Collected Publications of The IRPA Non-Ionizing Radiation Committee, Duchene et al. (ed)., 1991, Chapter 4, 53-66, 23 pages.

* cited by examiner

Opening for optical sensor around LED

A → optical sensor
B → LED (white)

Illustration of color sensor and detection of blood

Illustration of led/color sensor and detecting blood bioflorescence

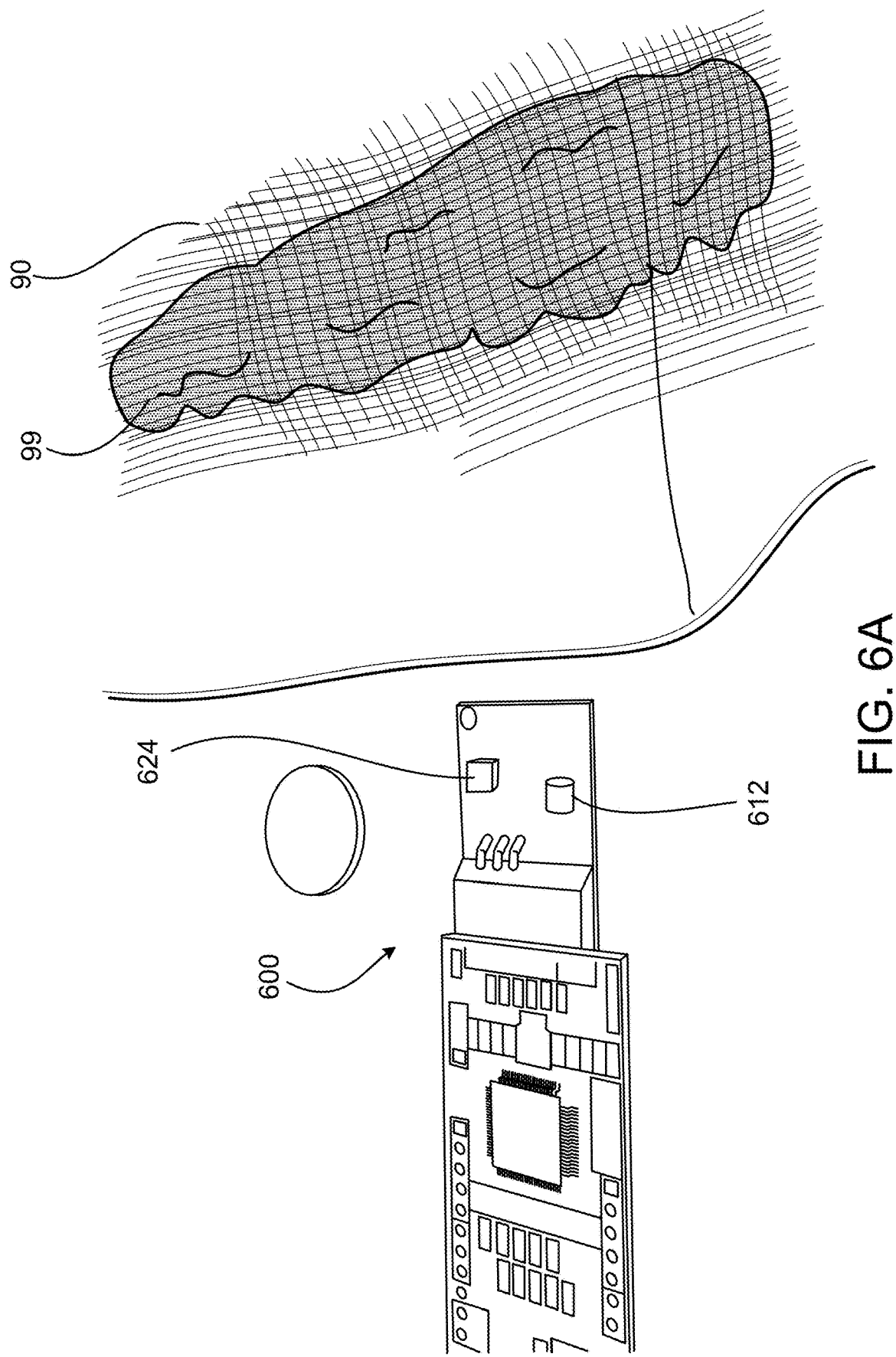

OPTICAL BLOOD DETECTION SYSTEM

BACKGROUND

Devices for detecting the presence of wetness and/or liquid leaks have a number of applications, including, for example, in mechanical systems, laboratories, experimental protocols, or devices having liquid lines, in use with those having enuresis or incontinence, or in those undergoing blood treatments. In particular, it is important to detect wetness due to blood leaks or other liquid line leaks during procedures that involve the removal of blood from a person, procedures like blood donation, blood detoxification, blood filtration/hemofiltration and hemodialysis. In hemodialysis, for example, blood is removed from a patient through a needle into a blood liquid line circuit that carries the blood to a hemodialysis machine that filters out waste toxins and removes excess water from the blood. With blood normally removed from the patient and through the blood liquid line circuit at a rapid rate, dislodgement of the needle or a break in the blood liquid line would lead to rapid and potentially fatal blood loss. For this reason, hemodialysis, which generally takes several hours and must be performed several times a week, is typically done in a medical setting where patients can be supervised. Patients must constantly be monitored visually by medical personnel for blood leaks so that, if needle displacement occurs, it can be identified and remedied before detrimental blood loss takes place.

SUMMARY

The present invention provides for an optical blood detector system that can sensitively and quickly detect the presence of a blood leak, for example, in a gauze around an intravenous injection site, and rapidly trigger an alert upon detection of the leak. Optical blood detection enables faster detection of blood compared to a traditional "wetness" detector because, in the traditional systems, blood must saturate the wetness detector in order for it to trigger a detection event. In contrast, a smaller amount of blood is able to be detected by an optical system. The blood detector system can be used in a number of situations and is particularly applicable in detecting a blood leak from the dislodgement of a needle in a patient undergoing an extracorporeal blood treatment (e.g., hemodialysis).

Aspects of the present invention include a blood detector system that rapidly detects the presence of blood by color change due to a blood leak in a system. The blood detector system may contain a reusable color sensor that is able to accurately detect color change and, in the case of an extracorporeal blood treatment, the presence of blood. In some embodiments, the entire system (e.g., a housing containing a detector and transmitter) may be roughly 30 mm in diameter, and configured to rest directly on gauze above a needle entry point in an arm. In some embodiments, the blood detector system quickly alerts both a user and medical personnel that a blood leak has been detected in a treatment system and, if necessary, halt the removal of liquids and/or blood from the patient. In some embodiments, if a color change from a leak is not detected for a period of time, the blood sensor enters a low power state, extending the life of the device and/or saving battery power. In some embodiments, the blood detector system monitors a number of locations simultaneously, which would, for example, eliminate the need for medical personnel to continuously inspect numerous patients visually for potentially fatal blood leaks due to needle dislodgement during an extracorporeal blood treatment.

In some embodiments, the system is configured to detect the color of blood, for example, a color change as blood is wicked into the gauze wrap. The color sensor detects a change in the light reflected from the gauze from white to red. In some embodiments, the detector employees LED, which is, in some embodiments, a white LED, to illuminate the area if needed. In some embodiments, the system detects blood by detecting one or more of the bio-florescent components of blood. For example, there are wavelength peaks of human blood appear at 274, 345, 415, 541 and 576 nm. Based on the analysis of fluorescence excitation-emission matrix, the major emission peaks of human blood occur at excitation-emission wavelength pairs of 260-630, 280-340, 340-460 and 450-520 nm, which are attributed to endogenous porphyrins, tryptophan, reduced nicotinamide adenine dinucleotide (NADH) or reduced nicotinamide adenine dinucleotide phosphate (NADPH), and flavin adenine dinucleotide (FAD), respectively. Accordingly, in some embodiments, an LED emits light at 450 nm, and the image sensor detects the corresponding bio-florescence emission of blood at 520 nm. In some embodiments, the color sensor is configured to detect the absorbance for hemoglobin from the reflected light to indicate the presence of blood. In these embodiments, the color sensor is configured to be responsive to Hemoglobin's a high absorption of wavelengths from 400 nm to 450 nm.

One embodiment is a blood detector system for detecting a blood leak at an intravenous injection site having a blood sensor with a support structure and a receiver unit in communication with the blood sensor. The blood sensor includes a color sensor attached to the support structure, the color sensor adapted to detect light from a sensing region adjacent to the color sensor, and the color sensor being configured to detect one or more of the reflected light of a frequency associated with blood and the emitted light associated with the bio-fluorescence of blood. The blood sensor also includes an electronic transmitter attached to the support structure, an antenna coupled to the electronic transmitter, and a power source connected to the processor, electronic transmitter, light emitting unit, and color sensor. The receiver unit includes a receiver for detecting one or more signal transmissions from the blood sensor, a controller in communication with the receiver, and an alert system in communication with the controller.

In some embodiments, the support structure includes an opaque region sized and positioned to occlude ambient light from directly reaching the sensing region.

In some embodiments, the color sensor includes an image sensor and a lens arranged to project an image of the sensing region onto the image sensor.

In some embodiments, the blood detector system includes a processor disposed in the support structure and in communication with the electronic transmitter and the color sensor, the processor being configured to determine the presence of blood in the sensing region based on the radiated energy of the reflect light detected by the color sensor.

In some embodiments, the processor is configured to determine whether the detected light is greater than a predetermined blood detection threshold value and a blood detection threshold value greater than the predetermined value indicates the presence of blood.

In some embodiments, the processor is configured to direct the electronic transmitter to transmit to the receiver unit in communication with the blood sensor at least one signal indicating that blood has been detected.

In some embodiments, the controller is configured to determine the presence of blood in the sensing region based the one or more signal transmissions from the blood sensor.

In some embodiments, the power source includes a rechargeable energy storage module or a replacement energy storage module.

In some embodiments, the blood sensor is adapted to be positioned adjacent to an absorbent material surrounding a needle insertion site, and the absorbent material includes the sensing region.

In some embodiments, the blood sensor includes an attachment device for attaching the blood sensor to a bloodline.

In some embodiments, the attachment device is adapted to position the color sensor above an entry point of an intravenous needle of the bloodline.

In some embodiments, the blood sensor includes a translucent cover positioned across the color sensor, the translucent cover sized and arranged to position the color sensor a distance away from the sensing region, the distance corresponding to a thickness of the translucent cover.

In some embodiments, the blood detector system includes a light emitting unit attached to the support structure and connected to the power source, the light emitting unit arranged to illuminate the sensing region.

In some embodiments, the light emitting unit is adapted to emit white light. In some embodiments, the color sensor is adapted to detect emitted light corresponding to major bio-fluorescent emission peaks of human blood. The detected major emission peaks of human blood may include at least one of 274 nm, 345 nm, 415 nm, 541 nm, and 576 nm. In some embodiments, the color sensor is adapted to detect light corresponding to the reflected color of human blood. In some embodiments, the light emitting unit is adapted to emit 450 nm light and the color sensor is adapted to detect light corresponding to absorption of the emitted light by the presence of hemoglobin in the sensing region.

In some embodiments, the emitted light includes light at 260 nm, and the color sensor is adapted to detect light at 630 nm. In some embodiments, the emitted light includes light at 280 nm, and the color sensor is adapted to detect light at 340 nm. In some embodiments, the emitted light includes light at 340 nm, and the color sensor is adapted to detect light at 460 nm. In some embodiments, the emitted light includes light at 450 nm, and the color sensor is adapted to detect light at 520 nm. In some embodiments, the transmission from the blood sensor of at least one signal of a blood detection is received by said receiver of the receiver unit and, in response to said at least one signal, the controller of the receiver unit triggers the alert system, and the alert system includes of one or more alarms selected from the group consisting of the display of a warning message, an audible alarm, a visual alarm and a physical alert.

In some embodiments, the color sensor includes red, blue, and green color sensing regions. In some embodiments, the color sensor includes white and infrared (IR) sensors. In some embodiments, the support structure is a printed circuit board, and where the color sensor and the light emitting unit are disposed on the printed circuit board. In some embodiments, the light emitting unit is a light emitting diode (LED).

Another embodiment is a blood detector for detecting a blood leak at an intravenous injection site includes a light emitting unit adapted to emit a light and illuminate a sensing region adjacent to the blood detector, a color sensor adapted to detect light from the sensing region, an electronic transmitter, an antenna coupled to the electronic transmitter, a processor in communication with the electronic transmitter and the color sensor, the microcontroller being configured to determine the presence of blood in the sensing region based on the color of the detected light and instruct the electronic transmitter to send an electric signal via the antennae to a remote receiver, the signal indicating the present of blood in the sensing region, and a power source connected to the processor, electronic transmitter, light emitting unit, and color sensor.

Yet another embodiment is a method of detecting a blood leak at an intravenous injection site includes attaching a blood sensor to an absorbent material surrounding a needle insertion site, the blood sensor including: a support structure, a light emitting unit attached to the support structure, the light emitting unit adapted to emit a light and illuminate a sensing region of the absorbent material, a color sensor attached to the support structure, the color sensor adapted to receive light reflected from the sensing region of the absorbent material, an electronic transmitter attached to the support structure, an antenna coupled to the electronic transmitter, a microcontroller in communication with the electronic transmitter and the color sensor, the microcontroller being configured to detect the presence of blood in the sensing region based on the color of the reflect light, a power source connected to the microcontroller, electronic transmitter, light emitting unit, and color sensor. After attachment, the color sensor detects the reflected light energy from the absorbent material and the microcontroller determines whether one or more properties of the reflected light energy are greater than a predetermined blood detection threshold value, and a blood detection threshold value greater than the predetermined value indicates the presence of blood, and directs the electronic transmitter to transmit to a receiver unit in communication with the blood sensor at least one signal that blood has been detected, whereby the receiver unit triggers an alert system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 6A and 6B are illustrations of a prototype blood detector system according to the invention and an absorbent material containing blood.

DETAILED DESCRIPTION

Figure 1A:
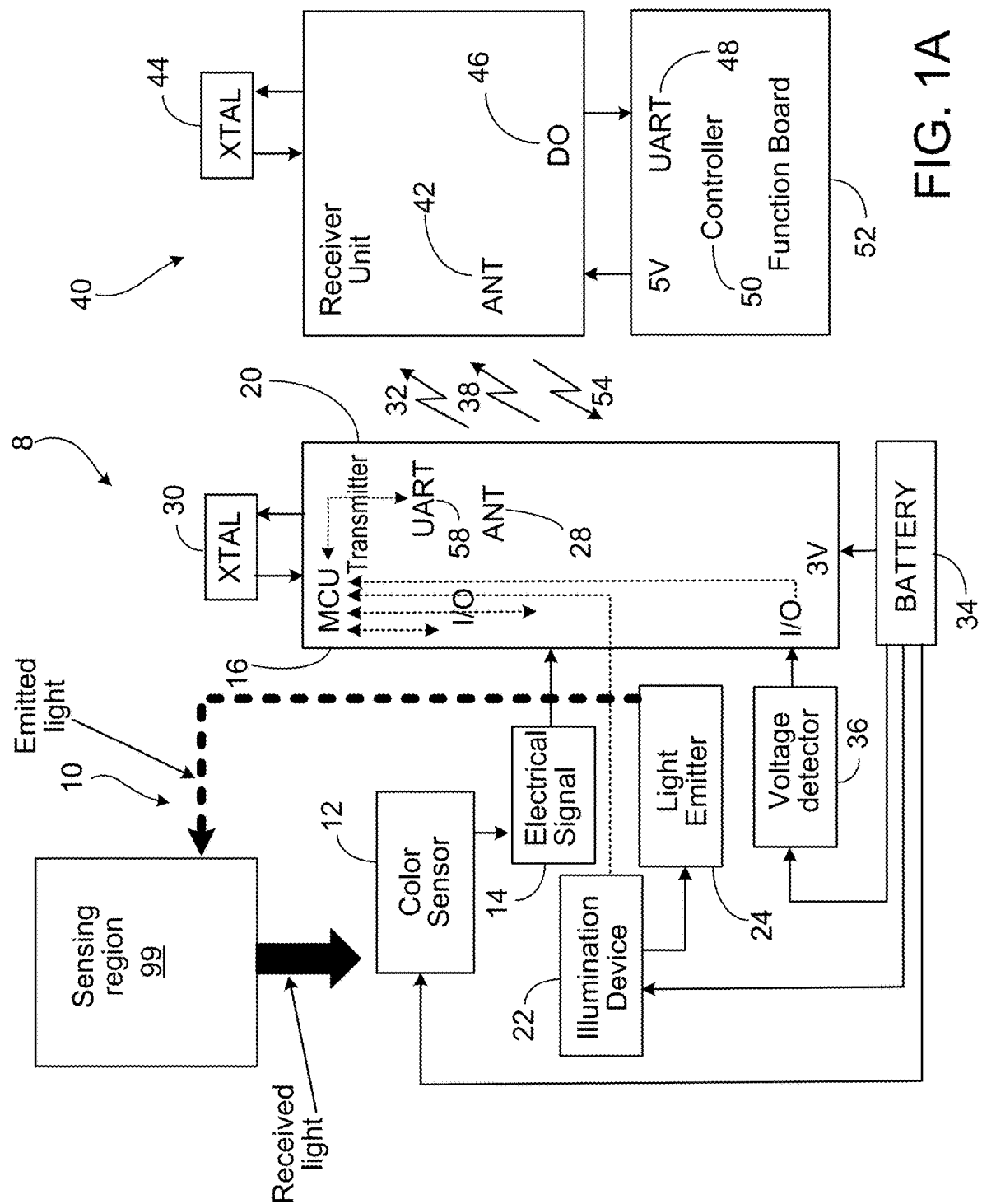
FIG. 1A is a schematic illustrating a blood detector system in which the receiver unit is integrated with a hemodialysis system operation unit.

A description of example embodiments of the invention follows.

Many devices have been proposed to detect wetness due to urine or blood or to detect the disconnect of a needle from a patient or a break/leak in a liquid line; however, these devices have several drawbacks. For example, many of the wetness detectors are not particularly efficient and, therefore, are mostly ineffective. Thus, they require too much moisture and/or liquid to trigger an alarm or there is too long of a delay between the occurrence of the wetness and the detection and/or alarm of the wetness. One example of a traditional wetness detection is disclosed in U.S. Pat. No. 7,605,710, which is incorporated by reference herein. In the case of hemodialysis, these deficiencies could be deadly; quick detection and alert is necessary in order to minimize blood loss due to the disconnect of a needle or a leak in a liquid line. Further, many proposed or existing devices are uncomfortable, unwieldy and, in the case in which an electric circuit is used to detect the moisture, can be unsafe if the patient is not properly protected from the electric circuit. Importantly, many devices are not appropriate to detect blood leaks that occur during extracorporeal blood treatments as the devices either cannot distinguish between blood and other bodily liquids or do not do so adequately. Consequently, the devices trigger a number of false alarms, a situation that substantially reduces the usefulness of the devices in a medical setting. In addition, many of the known wetness detection devices cannot themselves be physically reused, nor are their detection systems designed to be reset after wetness and/or moisture has been encountered.

Thus, there is a need for a wetness detection system that can rapidly detect wetness due to blood leaks and accurately identify any wetness that may be due to blood, especially in the instance of extracorporeal blood treatments. What is required is a detector that is sensitive enough to detect a small amount of blood in order to trigger an alert of a blood leak. There would also be a benefit to a blood detection system that could monitor a number of blood sensors simultaneously and one that has a number of different alarms at its disposal to alert both users and, where appropriate, medical personnel of blood and/or liquid line leaks. In the case of hemodialysis, this would free medical personnel from having to visually inspect a number of patients for blood leaks due to needle displacement or blood line breaks, allowing them to focus on other tasks. Further, it would be advantageous for the blood detector to be able to be reused and the blood detector system be easily reset after blood has been detected and/or an alarm has occurred.

As used herein, the term "blood leak" refers to any leak and/or moisture from the blood-containing/carrying components of a system, generally at a site of interface of those blood-containing components with other components of the system, or at a site at which blood is being removed from or returned to and/or infused into a patient. Thus, a blood leak could be a blood line leak and/or a needle insertion site leak, for example. To detect blood leaks, the blood sensor can be attached at any point to one or more components of a system. For example, the blood sensor can be in close proximity to an opaque blood line entry point/needle insertion site or attached to a material surrounding a blood line entry point/needle insertion site of a blood line of the system. The blood line may be a small-sized (e.g., micro-sized) tubing, this type of tubing generally including a polymer (e.g., plastic) having properties (e.g., minimal drag and/or liquid adsorption, non-reactive, non-corrosive, non-degradable) that make it well-suited for carrying the desired liquid. In a particular embodiment, the system is an extracorporeal blood treatment system in which the blood sensor is attached to various blood lines of the system to detect leaks in, for example, a line for carrying blood. The blood sensor attachment device for attaching the blood sensor to a blood line, for example, can be any device that can be attached to the blood sensor and used to securely attach the blood sensor to a blood line of the system including a clasp, coupling, pin, clip, bonding material (e.g., tape, glue) or the like. In some instances, the blood sensor is positioned/placed on the absorbent material above an intravenous needle injection to immediately detect in the absorbent material that leaked from the injection site.

Certain aspects of the present invention relate to a system for detecting the presence of blood, in particular, blood due to a blood leak into an absorbent material positioned around an intravenous injection site. Examples described herein include an optical blood detector system with a blood sensor, an attachment device for attaching the blood sensor to the components of the system, and a receiver unit in communication with the blood sensor. The blood sensor may include a support structure containing an electronic transmitter, an antenna coupled to the transmitter, a color sensor, and a power source for the electronic transmitter and the color sensor. The color sensor is positioned to receive reflected or emitted light from a sensing region adjacent the color sensor and sense the presence of blood in the sensing region based on the properties of the detected reflected or emitted light. In some instances, the blood sensor includes a microcontroller in communication with the electronic transmitter. In some instances, the blood sensor includes a light source attached to the support structure and arrange to illuminate the sensing region. In some instances, the microcontroller controls the operation of the color sensor and the light source. In some instances, the microcontroller receives a signal from the color sensor and executes instructions to determine if the signal indicates the presence of blood in the sensing region. In other instances, the microcontroller receives the signal from the color sensor and operates the electronic transmitter to send the signal via the antenna to a remote receiving device configured to detect the present of blood in the sensing region based on the received signal.

In some embodiments, an alternative configuration of the blood detector system used as a bacterial detection system. The blood sensor may be placed adjacent to a dialysis fluid window for detecting the bio-fluorescence of bacteria. Accordingly, a bacterial infection in the peritoneum or at the catheter site could be detected preventing a possible major infection for the patient.

Thus, in a particular embodiment shown in FIG. 1A, a blood sensor 122 is attached to a wound dressing covering a needle insertion site and the blood sensor 122 sends a signal 124 of a blood leak through wires 128 or wirelessly via an antenna 126 to a receiver unit integrated with the hemodialysis treatment operation unit 120. In this embodiment, the transmission of the blood leak signal 124 triggers an audible alarm 130 that emanates from an alarm device located beneath hemodialysis operation unit 120. Further, in the instance that the receiver unit is integrated with an extracorporeal blood treatment system like a hemodialysis system, in response to the signal of a blood leak, a controller 50 can be configured to direct the extracorporeal blood operation unit to stop the blood pump(s) and close one or more valves along the blood line(s) through which blood is drawn from and/or returned to the patient.

Figure 1B:
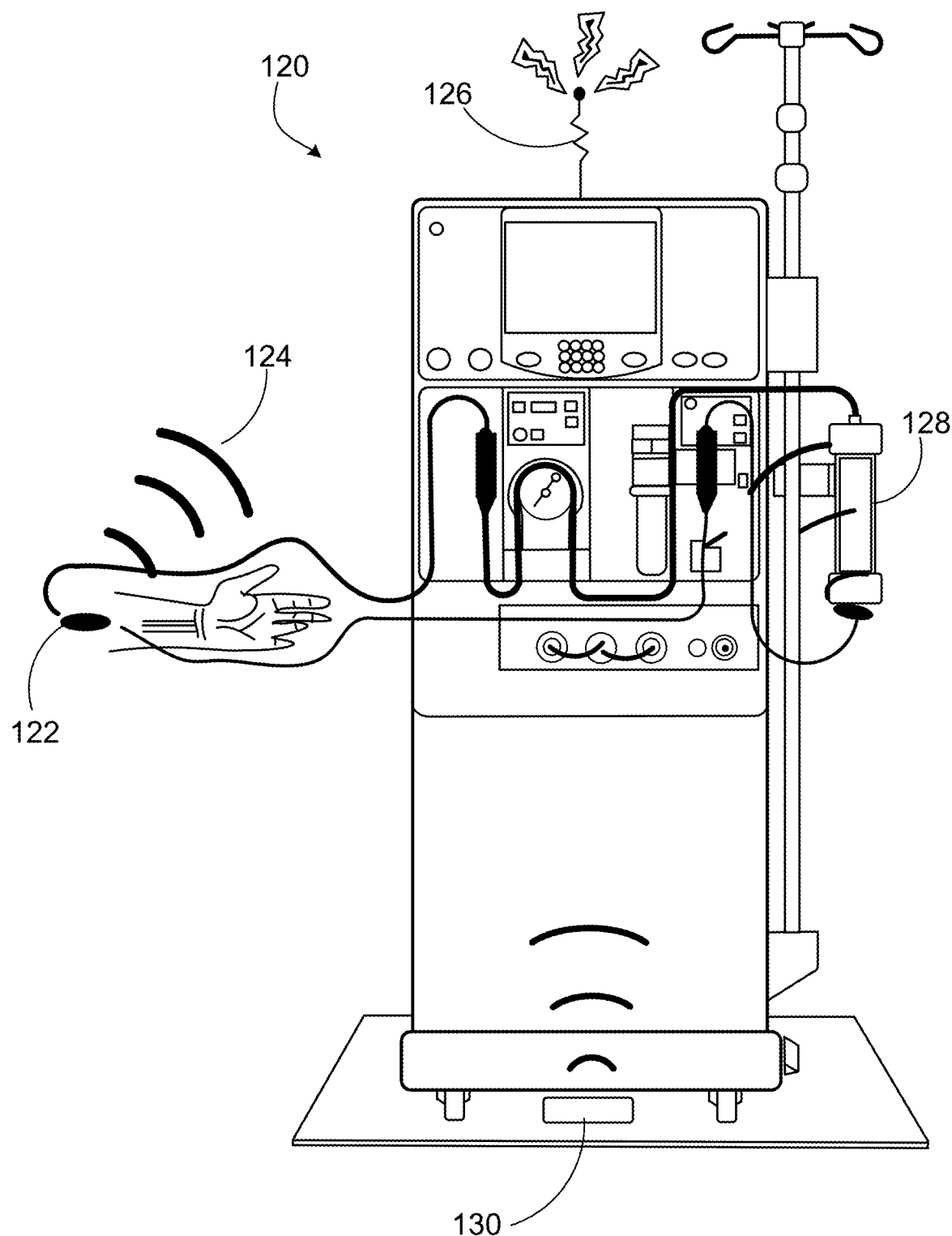
FIG. 1B is a block diagram illustrating a blood detector system according to the invention.

Accordingly, shown in FIG. 1B is a blood detector system 8 that includes a blood sensor 10 and a receiver unit 40. The blood sensor 10 of the blood detector system 8 is generally small and, in some instances, is watch-sized. The blood detector 10 includes a color sensor 12 configured to detect blood using an optical detection of light reflected or emitted from a sensing region to which the color sensor 12 is exposed. Thus, the blood detector system 8 can be used to detect any liquid that is colored, fluorescent, bio-fluorescent, or any liquid that changes the color of the light reflected or emitted from a material when the liquid is absorbed in the material. In some instances, the color sensor 12 is an imagine sensor or a simple 3-detector matrix of a single red, blue, and green detector so long as the reflect color or emitted light of the liquid results in a change in the color of light incident on the sensing region. For example, the color sensor 12 could be a basic red, blue and green color detector such that corresponding red, blue and green color components of the reflected or emitted light energy from the sensing region are measured by each detector region, thereby generating color profile of the reflected or emitted light that can be compared to values associated with blood or other liquids. In another example, the color sensor 12 may be an image sensor with a lens arranged to project an image of the sensing region onto a plurality of pixels of the color image sensor 12 to detect both the color, size, and location of a blood in the projected image of the sensing region. In some instance, the color sensor detects a change in the light reflected from the gauze from white to red. In some instance, the detector employees LED, which is, in some instances, a white LED, to illuminate the area if needed. In some instances, the system detects blood by detecting one or more of the bio-florescent components of blood.

In yet another example, the color sensor could be a light energy sensor configured to detect a one or more specific wavelength of light associated with the reflected light energy of blood from a light source of a known color spectra or, alternatively, configured to detect one or more wavelengths associated with the emitted light energy of blood in response to a bio-fluorescent excitation by a light source. Bio-florescence is the emission of light from tissue/cells/DNA etc. when excited by an external light source. Configured a color sensor using a narrow band wavelength reduces noise from objects and/or items that are of no interest. For example, wavelength peaks of human blood appear at 274, 345, 415, 541 and 576 nm. Based on the analysis of fluorescence excitation-emission matrix, the major emission peaks of human blood occur at excitation-emission wavelength pairs of 260-630, 280-340, 340-460 and 450-520 nm, which are attributed to endogenous porphyrins, tryptophan, reduced nicotinamide adenine dinucleotide (NADH) or reduced nicotinamide adenine dinucleotide phosphate (NADPH), and flavin adenine dinucleotide (FAD), respectively. Accordingly, in some instances, an LED emits light at 450 nm, and the image sensor detects the corresponding bio-florescence emission of blood at 520 nm. In some instances, the color sensor is configured to detect the absorbance for hemoglobin from the reflected light to indicate the presence of blood. In these instances, the color sensor is configured to be responsive to hemoglobin's high absorption of wavelengths from 400 nm to 450 nm.

The exposure of the color sensor 12 to light energy leads to the generation of a detectable electric signal 14 that is sent to a microcontroller 16. In some instances, the electric signal is processed by the microcontroller 16 to determine if the color sensor 12 has detected blood, but in other instances the microcontroller is configured to transmit a corresponding signal to a remote processor for determining if the color sensor has detected blood in the sensing region. Thus, the blood sensor 10 may be configured to detect blood or configured to relay color information to a remote processor. The microcontroller 16 can be any device that meets the general specifications of an MCU, that is, one that contains all the necessary functional components of a computer (e.g., central processing unit (CPU) core, program memory (ROM or flash), data memory (RAM), external peripherals, complementary resource and input/output (I/O) interfaces to communicate with the peripherals). Microcontroller architectures are commercially available from a number of sources (e.g., producers such as IBM/AMCC, Atmel, Cypress MicroSystems, Freescale Semiconductor, Fujitsu, Holtek, Hitachi, AVR, Infineon, Intel, Microchip, National Semiconductor, Texas Instruments, Toshiba, and others). Based on the measurement of the color sensor signal 12 generated, the microcontroller 16 determines if the color signal is above a blood threshold value such that a color signal above a detection threshold value indicates the presence of blood in the sensing region. One having skill in the art can specify the appropriate threshold value at which the microcontroller 16 determines that the light from the blood to which the color sensor has been exposed meets the criteria of "blood" based on the particular microcontroller parameters and the desired sensitivity of detection (e.g., for a particular application and/or patient(s). In some instances, the threshold value is a percent change in the sensed color of the received light from the sensing region. In some instances, the threshold value is a color ratio between two or more colors of the sensed colors of the received light from the sensing region. In some instances, the threshold value is a minimum value of one or more specific light frequencies sensed in the received light from the sensing region. The one or more specific light frequencies associated with the minimum detection levels could be, for example, frequencies corresponding to the bio-fluorescence of blood or frequencies corresponding to an absorption curve of one or more substances in blood. In some instances, the threshold value is a function of the light output of the illumination device or, in some instances, is a function of the sensed light energy from the sensing region during operation.

The blood sensor 10 can be further includes of a color sensor 22 that includes an illumination 22 device for detecting the presence of blood. In a particular embodiment, the blood sensor 10 identifies a blood leak associated with the dislodgement/displacement of a needle used in removing and/or returning blood to a patient during an extracorporeal blood treatment. Thus, the blood sensor 10 may be attached to an absorbent material surrounding a needle insertion site such that it is in close enough proximity to the site to quickly detect any blood that has leaked from the site. In some instances, the blood sensor 10 is within a few centimeters of where the needle has been inserted in a patient's vein and/or artery. The material surrounding the needle insertion site can be any absorptive material (e.g., absorbent pad, foam, cloth, paper) appropriate for medical use (e.g., sterile) and in some instances, is a sterile wound dressing (e.g., gauze, mesh, Band-Aid). Accordingly, the blood sensor 10 is able to detect the absence of blood by received a light signal in close agreement with the light emitted by the illumination device.

In this manner, the blood sensor can be configured to detect a blood leaks or various rates depending on the threshold of detection.

The illumination device 22 is connected to a power source 34 of the blood sensor 10 and is also in communication with the microcontroller 16. The illumination device 22 can include a light source 24 produces/emits light in the visible, ultraviolet, or near-infrared spectrum, or any spectrum of light allowing for the specific identification of the blood present. In some instances, the light source the light source 24 is a light emitting diode (LED). In one embodiment, the illumination device 22 of the blood detector 12 is on constitutively, emitting light at some constant interval (e.g., every 10 seconds). Alternatively, the illumination device 24 could be trigged by the color sensor 22, such that, in some instances, the color sensor 12 senses a lower illumination condition, possible from the color sensor 22 being place against the absorbent material on a patient underdoing an intravenous injection and signals the illumination device 24 to illuminate the darkened sensing region. In some instances, the illumination device 22 could be trigged by a button (not shown) on the blood sensor 10. In some instances, the illumination device 22 includes a light source 24 with the ability to emit light in multi different frequencies, and the frequencies could be cycled to improve blood detection. In a particular embodiment, in response to the color sensor's 10 detection of blood, the microcontroller 16 directs the illumination device 22 light source 24 to emit light, or emit light in a different frequency, in order to confirm if the color sensor's initial detection is blood. The light emitted by the light source 24 allows for the specific identification of the blood present due to differing structural properties of different molecules. Thus, different molecules absorb light at distinct wavelengths and, consequently, knowledge of the absorbance spectrum of a particular molecule and/or substance allows for that substance to be identified by its spectral signature. Accordingly, the absorbance spectrum of the primary light-absorbing molecules of blood, oxyhemoglobin and deoxyhemoglobin, is known, making a signal due to blood distinguishable from a signal due to some other liquid (e.g., sweat). The illumination device 22 can produce light using any appropriate light source (e.g., a halogen or tungsten lamp), and may produce visible light, ultraviolet, or near-infrared light using a light-emitting diode (LED), so long as the light source produced is safe for use on humans (see Duchlne A S, et al., IRPA Guidelines on Protection Against Non-ionizing Radiation. Toronto, Ontario, Canada, Pergamon Press Canada, Ltd. 1991, pg. 53-66). Light emitted by the illumination device 22 and absorbed by the blood present causes the generation of a detectable light energy emission of a wavelength that is captured by a wavelength-calibrated photodiodes of the color sensor 12. The wavelength or light energy information detected and captured by the color sensor 12 is received by the microcontroller 16. As detailed above, the light energy received by the color sensor 12 may be light energy reflected or scattered (e.g., Rayleigh scattering) from blood in the sensing region 99 (as described below with respect to FIGS. 3A and 3B), or may be light energy emitted through bio-fluorescence of blood in the sensing region 99 in response to specific emitted frequencies of the light emitted by the light source 24 of the illumination device.

In the instance where blood is not detected by the color sensor 12 for a specified period of time, the microcontroller 16 can direct the blood sensor 10 to enter a low power state, thereby elongating the life of the power source of the blood sensor 10 by, for example, reducing the drain of the power source. Thus, when there is a lack of a wavelength (e.g., color intensity above a threshold value) measurement for a specified amount of time, the microcontroller 16 causes the blood sensor 10 to enter a low power state for a specific interval of time, the specified amount of time and specific interval of time measured by a clock internal to and/or associated with the microcontroller 16. The amount of time that elapses without blood detection before the blood sensor enters a low power state and the interval of time the blood sensor remains in a low power state is best determined by one having skill in the art, these time periods alterable through the programming of the microcontroller 16. For instance, the skilled artisan could alter the time periods (e.g., before entry into a low power state and the duration of the low power state) according to field testing or based on use of the blood sensor in clinical practice. The ability of the blood sensor 10 to enter a low power state can be due to several actions including reducing power to the color sensor 12, the microcontroller 16 (e.g., by halting the execution of non-essential MCU functions) and/or the illumination device 22 if the light source 24 turns on at regular intervals without an electrical signal and/or direction from the microcontroller 16.

The blood sensor 10 also includes a transmitter 20 connected to antenna 28, transmitter 20 generating and/or modulating a signal wave that transmits a blood leak signal to receiver unit 40. Thus, in response to an indication of blood present, the microcontroller 16 directs the transmitter 20 to send a signal 32 via the antenna 28 that a blood leak has been detected by blood sensor 10. The blood leak signal transmission encompasses a communication that includes not only the signal of a blood leak, but also other pertinent information (e.g., blood detection signal, wavelength value, power levels, sensor functionality); alternatively, the data stream containing other information can be transmitted separately. The transmitter 20 can be any appropriate transmitter (e.g., amplitude-shift key [ASK]) and can also be separate from the microcontroller 16. However, in some implementations, the microcontroller and transmitter are integrated into one functional unit (e.g., rfPIC12F675F). In this case, the microcontroller can have an external crystal to generate transmission frequencies (e.g., 13.56 MHz).

In order to send a signal of a blood leak to receiver unit 40, the blood sensor 10 can be wired to a receiver unit 40 such that blood leak signal 32 is transmitted to a receiver unit 40 over hardwire(s). In a particular embodiment, the blood leak signal 32 is transmitted to the receiver unit 40 wirelessly with the data encoded for wireless transmission (e.g., using pulse width modulation). Wireless communication can be through any suitable wireless data network or can be through a wireless communication link (e.g., using protocols such as Bluetooth, ZigBee). Overall, any wired or wireless data transmission network can be used for communication between the blood sensor and the receiver unit. Accordingly, in response to an indication that the blood sensor 10 has been exposed to blood, the transmitter 20, in some instances, generates a signal wave in the near-infrared band using an infrared (IR) device 24. In other instances, the transmitter 20 is a radio frequency transmitter generating a radio frequency signal. The radio frequency (RF) signal can then radiate and propagate blood leak signal 32 by antenna 28 over a selected frequency to receiver unit 40. A crystal oscillator 30 creates a precise, stable frequency over which blood leak signal 32 can be transmitted and typically resonates at some standard frequency (e.g., 10, 20, 40 MHz); however, in some implementations the crystal oscillator transmits at a frequency of 433.92 MHz crystal oscillators (XO) can be further used as a precise clock to enable a particular type of signal transmission (e.g., synchronous serial transmission or asynchronous transmission) from the blood sensor 10 to receiver unit 40. In some instances, the crystal oscillator 30 is also utilized for signal processing, sleep mode, and general operation of the blood sensor 10. There are numerous types of crystal oscillators that can be used in the blood detector system 8 (e.g., microcomputer-compensated (MCXO), oven-controlled voltage-controlled (OCVCXO), oven-controlled (OCXO), rubidium (RbXO), temperature-compensated-voltage controlled (TCVCXO), temperature-compensated (TCXO) and voltage controlled (VCXO)). The type of signal transmission (e.g., continuous or idle) may be chosen by one having skill in the art as being most appropriate for the conditions of use and may be one that complies with industry standards (e.g., RS232-C, CCITT). In some instances, the crystal oscillator design reduces environmental effects (e.g., temperature, humidity, pressure and vibrations) for better frequency stability. The duration of the signal transmission can be any desirable length and in a particular embodiment, the duration of the signal transmission is 100 milliseconds (msec). At least one signal that a blood leak has been detected can be transmitted at every specified interval of time dependent, for instance, on the length of signal transmission. In some implementations, two signals in a row are transmitted every 60 seconds which could also distinguish the two blood leak signals from other baseline and/or other data transmissions. In order to quickly alert a user (e.g., subject, patient and/or medical personnel) that a blood leak has occurred before significant blood loss, particularly blood loss, can take place, it is envisioned that blood sensor 10 detects blood and transmits the signal of a blood leak to a receiver unit within a few seconds of an indication that blood is present.

The receiver unit 40 of the blood detection system 8 that receives the blood leak transmission from the blood sensor 10 includes a receiver for detecting a signal transmission from the blood sensor, a controller 50 in communication with the receiver and an alert system in communication with the controller. Receivers are commercially available, for example, MICFO22BM from Micrel. Thus, antenna 42 of the receiver unit 40 receives the blood leak signal 32 transmission 32 from the blood sensor 10 that a blood leak has been detected over a matching frequency (e.g., 433.92 MHz) that is generated by the crystal oscillator 44 of the receiver unit 40. A data output interface (DO) 46 on the receiver provides to controller 50 the data which is transmitted from blood sensor 10 to the receiver. In one embodiment, the receiver unit 40 can be in communication with one or more blood sensors. In this case, wireless communication/signal transmission between the one or more blood sensors 10 and the receiver unit 40 is most advantageous. In order for the receiver unit 40 to accurately monitor transmissions from more than one blood sensor 10, it would be necessary for each blood sensor 10 to transmit unique identification information, typically a unique identification (ID) number stored in the microcontroller memory (e.g., dynamic random access memory (DRAM), static random access memory (SRAM), electrically erasable programmable read only memory (EEPROM) or other storage medium(s)), the ID transmitted to the receiver unit 40. The receiver unit 40 would then, in turn, need to include a device and protocol to learn, store and track this unique ID information (e.g., an appropriately programmed microcontroller). In some instances, the alert system for each blood sensor 10 would be reset when the receiver unit initially receives transmission of a unique ID from each of the blood sensors. To perform its various functions, receiver unit 40 would either be connected to a power source (e.g., AC or DC) or further including a power source such as a rechargeable energy storage module or a replacement energy storage module (e.g., a battery). Alternatively, the receiver unit 40 could be integrated with a system like an extracorporeal blood system operation unit which performs various blood treatment functions (e.g., blood oxygenation, detoxification, transfusion or filtration). Thus, the controller 50 would be a central computer controlling the system of the extracorporeal blood treatment unit including functional board 52 of the system unit. In this case, the receiver unit 40 would be powered by the power source of the extracorporeal blood treatment system unit and interface with the system controller. In some implementations, the receiver unit of the blood detector system is integrated with a hemodialysis treatment system unit.

Accordingly, in response to at least one signal transmission 32 from at least one blood sensor 10 that a blood leak has been detected, the controller 50 (e.g., one or more computer processors) receives the signal communication from the receiver DO 46 via a universal asynchronous receiver-transmitter (UART) 48, the UART microchip providing an interface for the controller to the receiver. Thus, the UART 48 receives serial bits of data from the receiver and converts the bits into complete bytes that are interpretable by controller 50. A number of UART devices are available (e.g., 8250, 16550) and, in some instances, the UART provides some amount of buffering of the data (e.g., 16550 UART) so that the data can be cached, reassembled and reorganized before being sent to the controller. The controller 50 can then trigger the alert system indicating that a blood leak has been detected by a particular blood sensor 10. For example, the controller 50 can deliver a warning message that is displayed either on the receiver unit (if distinct) or on the functional board of an extracorporeal treatment system operation unit, for instance. In addition, the controller 50 can trigger one or more alarms that are audible, visual or physical. The alarms can be any known audible (e.g., a high volume sound, bell, siren, horn, buzzer, beep, whistle, recording or voice) or visible (e.g., colored, flashing, strobe, fluorescent or halogen light) alarm. If the blood detector system 8 is used to detect blood leaks in some sort of treatment system (e.g., an extracorporeal blood treatment system), a physical alarm can also be employed to warn the patient/user. For instance, the controller 50 can cause a blood pressure cuff attached to a patient's arm to squeeze the patient's arm, thereby waking and/or alerting the patient. Similarly, a device capable of vibration could be attached to a patient (e.g., on a blood pressure cuff) and the controller 50 could cause the device to vibrate rapidly and/or audibly so that the user would be alerted.

In another embodiment of the blood detector system 8, the blood sensor 10 can further include a receiver (sensor receiver) and receiver unit 40 can further include a transmitter (receiver transmitter) such that there can be two-way communication between the blood sensor 10 and the receiver unit 40. Two-way communication between the receiver unit 40 and the blood sensor 10 is advantageous as it allows the receiver unit 40 to send a number of communications to the blood sensor(s) 10 including software updates, inquiry into configuration settings, and reconfiguration of sensor settings and/or determination of the number of times the blood sensor 10 has been used. Further, as one-way signal transmissions from the blood sensor 10 to the receiver unit 40 can be easily interrupted by interference from other devices, particularly in a medical setting, two-way communication can be utilized to ensure that blood leak signal 32 transmissions from the blood sensor(s) 10 are received by the receiver unit 40. Thus, the receiver unit 40 could transmit an acknowledgement communication back to the blood sensor 10 after it has safely received a blood leak signal 32 transmission. In addition, two-way communication would be useful in enabling the receiver unit 40 to ascertain if the blood sensor is functional. Accordingly, in one embodiment, a transmitter of receiver unit 40 sends a functionality inquiry test signal 54 to at least one blood sensor 10 at every specified interval of time (e.g., every 60 seconds). Functionality test signal 54 is received by a blood sensor 10 receiver and the data converted by UART 58 for the microcontroller 16. In response to functionality test signal 54, the microcontroller 16 of an operational blood sensor 10 directs the blood sensor transmitter 20 to send a functionality confirmation signal back to receiver unit 40, the transmission of the signal indicating to the receiver unit that the blood sensor is functional. The number of such communications can be varied (e.g., two or more transmissions) per specified interval of time. In some instances, the blood sensor 10 also retains an ability to receive the functionality test signal 54 and transmit a functionality confirmation signal in response while in a low power mode that has been initiated by the microcontroller 16 (e.g., in response to a lack of an electric signal and/or blood detection). Two-way communication could also allow receiver unit 40 to direct one or more blood sensor(s) 10 to enter a low power state. Thus, if there has been no transmission of a blood leak signal 32 from blood sensor(s) 10 for a specific interval of time (e.g., 2.5 minutes) and receiver unit 40 has received a functionality confirmation signal from blood sensor(s) 10, then receiver unit 40 could transmit a signal to blood sensor(s) 10 directing the one or more blood sensor(s) to enter a low power state for a specified amount of time (e.g., 15 seconds).

Advantageously, the alert system of the blood detector system 8 can easily be reset after one or more alarms have been triggered by the blood sensor(s) 10, one or more alarms that include the display of a warning message, triggering of visible, audible or physical alarms, or the stopping of the extracorporeal blood treatment via the halting of blood pump(s) and/or closing of blood line valves. Thus, the blood sensor 10 can further include a reset device that returns the sensor to a state in which the microcontroller 16 does not perceive and/or indicate the presence of existing and/or past blood. In a further embodiment, the blood sensor 10 could be reset by the receiver unit 40 if two-way communication is employed. In this case, an external operator (e.g., medical personnel) could, through an input device that is on (e.g., dials, buttons, keys, switches or the like) or in communication with (e.g., a remote) receiver unit 40 and/or functional board 52, direct controller 50 to transmit a signal to blood sensor 10 that instructs the microcontroller 16 to reset any indications of blood and/or blood. In another embodiment, blood sensor 10 can be programmed such that if the blood detector system 8 is reset a specified number of times (e.g., three times) within a specific amount of time (e.g., ten minutes), then, in the event of any subsequent blood leak signals, the full alert system is not triggered. Instead, the next blood leak signal causes the display of a warning message only on the receiver unit/treatment system. The blood sensor 10 could also be reset by the user or any medical personnel through direct interaction with the blood sensor, by pressing a reset button on the sensor for example.

In some instances, the blood detector system 8 also has a number of safeguards to ensure that the blood detector 10 is able to detect blood and/or blood or has adequate power to do so. For instance, before being used on a patient, the blood sensor 10 can be self-tested, in some instances after its initial location and/or identification by the receiver unit. Thus, upon the placing a test card or other sample to mimic the color or bio-fluorescence of blood in the sensing region of the color sensor 12, the blood sensor 10 would send an initial signal to a receiver that the color sensor 12 is functional for blood detection. In response to this initial signal from the blood sensor 12, the receiver unit 40 may display a message on the receiver unit and/or extracorporeal blood system operation unit that the blood detector(s) 10 is functional. Further, to alert a patient and/or medical personnel of a limited energy status of the blood sensor 10 power source 34 (e.g., less than 10% of the life of a battery), the blood sensor 10 can further include a low power alarm circuit. Thus, the power source of the blood sensor 10 is a battery 34, (having 3 volts), which is connected to the voltage detector 36, the voltage detector in communication with the microcontroller 16. When the voltage measured by voltage detector 36 is less than a specified voltage (e.g., 2.2 volts), the microcontroller 16 triggers a low battery alarm. A low battery alarm would only be triggered in the instance that the presence of blood is not also indicated by the blood sensor 10. The low battery alarm can be an audible and/or visual alarm located on the blood sensor 10 itself or integrated with the receiver unit and/or an extracorporeal blood treatment system unit. In the case that the alarm is located on the blood sensor 10, the audible alarm could be a sound produced by the microcontroller 16 and the visual alarm could be a small, low-powered LED directed to be turned on by the microcontroller 16. Alternatively, or in addition to any alarm on the blood sensor 10 itself, the microcontroller 16 can direct the transmission of one or more signals 38 to the receiver unit 40 that the voltage of the battery 34 is low. In response, the controller 50 of the receiver unit 40 can display a warning message and/or trigger one or more visual or audible alarms. In some instances, the low battery warning message and alarm(s) differ in text, sound, volume and/or intensity from the one or more alarms of the blood leak alert system.

Figure 2A:
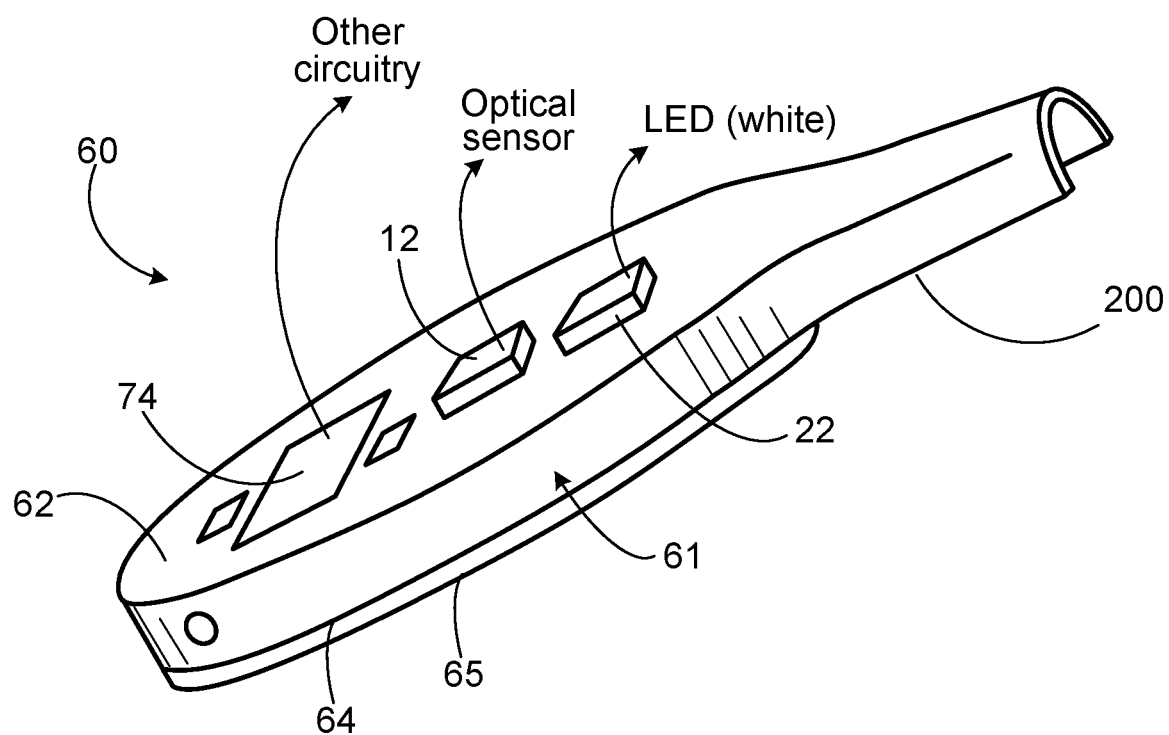
FIGS. 2A-2C are illustrations of a prototype of a blood sensor according to the invention.
Figure 2B:
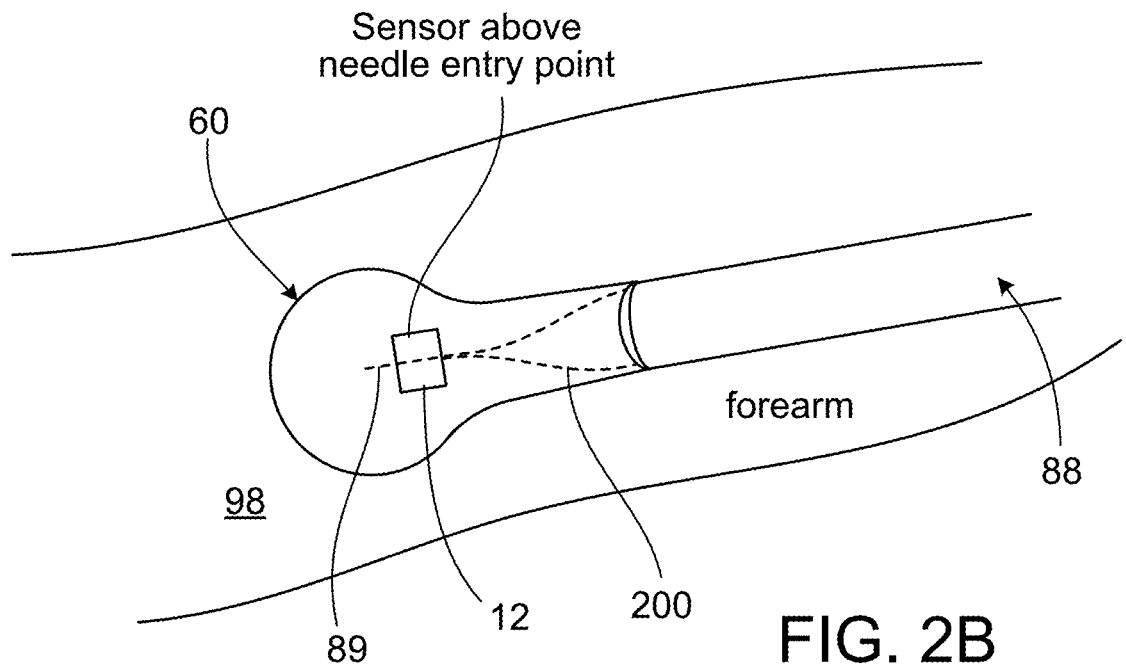
Figure 2C:
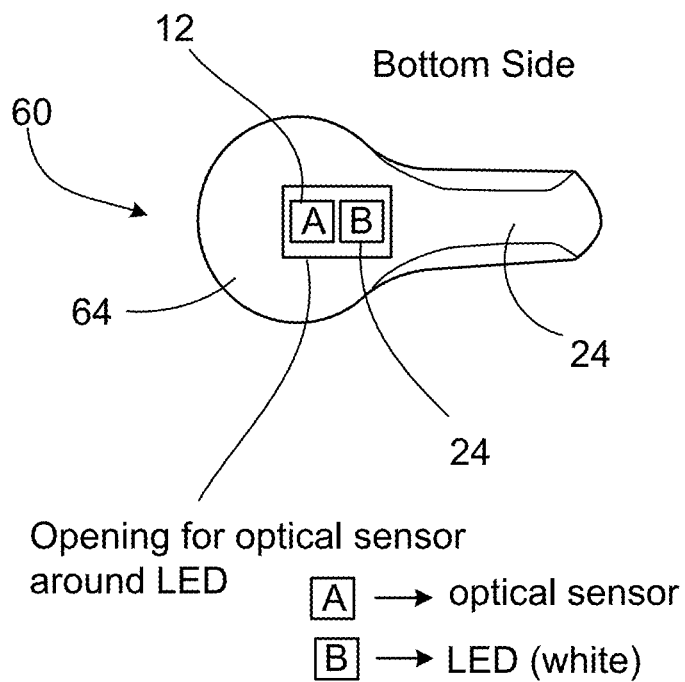

FIGS. 2A-2C are illustrations of a prototype of a blood sensor according to the invention. A prototype of a blood sensor device, featuring a color sensor 12 and an illumination device 24 as described is shown in FIGS. 2A-2C. A blood sensor 60 includes a solid support structure 61 having a portion (e.g., a second portion) with first side 62 and a second side 64 and can be activated and/or turned on by an initial toggling of a switch (not shown) on the blood sensor 60, a wireless signal, or the exposure of the color sensor 12 to a specific light signal. The solid support structure 61 including the blood sensor 60 generally would be a material that does not conduct electricity (e.g., an insulator) and, in a particular embodiment, is a potting compound (e.g., FR-4, a resin reinforced with a woven fiberglass mat) that holds the components of the sensor and/or makes up the sensor bulk surrounding sensor components and, if desired and/or necessary, can include a thermally conductive layer between sensor components to dissipate heat (e.g., heat generated by the illumination device). The solid support structure 61 includes a portion (e.g., a first curved portion) with a clip 200 to attach the blood sensor 60 to a blood line 88. In some instances, the solid support structure 61 includes a transparent cover 65 positioned over the second side 64 of the solid support structure 61 to offset the placement of the second side 64 from a sensing region. In this manner, the transparent cover 65 enables the illumination device 22 and the color sensor 12 to be positioned a consistent distance away from the sensing region. In some instances, the solid support structure 61 is opaque and is sized and positioned with respect to the clip 200 to occlude ambient light from reaching the sensing region. In this manner, the solid support 61 ensure that the color sensor 12 is primarily detecting light energy resulting from the light spectrum of the illumination device 22. The color sensor 12 and illumination device 22 could be excited/powered by any AC or DC power source that produces enough power to operating the color sensor 12 and illumination device 24 for the duration of a typical observing period and be able to transmit a wireless signal consistently during the observing period. In some instances, the power source is small enough to fit inside the blood sensor 60 itself.

Attached to first surface 62 of the blood sensor 60 is the microcontroller/transmitter unit 74 and antenna (not shown). Although several types of antennas could be used to transmit a blood leak signal, in some instances, the antenna is electrically small (e.g., physically small with respect to wavelength) and is, for example, a printed circuit board (PCB) loop antenna or trace antenna. A battery, acting as a power source for the blood sensor 60, is also within the device 60. The battery for use in the blood sensor of the invention can be a wide variety of batteries (e.g., lithium, lithium ion, nickel cadmium, zinc carbon, alkaline, nickel metal hydride, nickel iron, nickel zinc or specialty battery) and is best selected by the skilled artisan for the particular design and usage of the blood sensor. In some implementations, the battery is a coin-sized lithium battery (e.g., CR2032) as these types of batteries are small, long-lasting, light-weight and have higher, more stable voltage profiles.

A schematic of the placement of the blood sensor 60 is shown in FIG. 2B. For the detection of blood around the intravenous injection site 98, the blood sensor 60 is attached using clip 200 to a blood line 88, with the bottom side 64 of the blood sensor 60 positioned such that the color sensor 12 is above the insertion point of a needle 89 of the blood line. FIG. 2C is a view of the bottom side 64 of the blood sensor 60, showing the location of the color sensor 12 and illumination device. The bottom side 64 includes an opening (e.g., a recess) for the optical sensor around the LED.

Figure 3A:
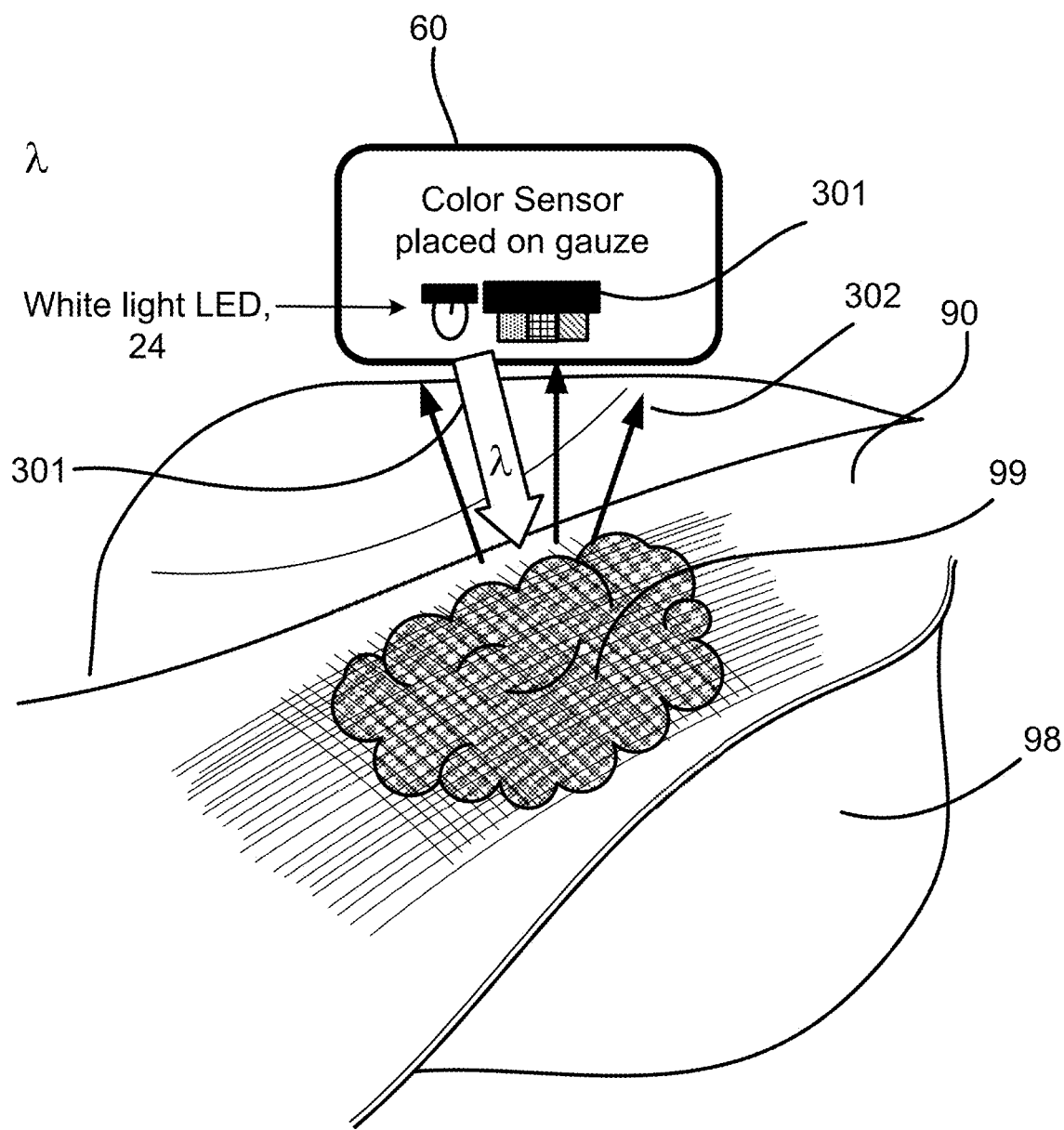
FIGS. 3A and 3B are illustrations of the detections method of a color sensor and illumination device according to the invention.
Figure 3B:
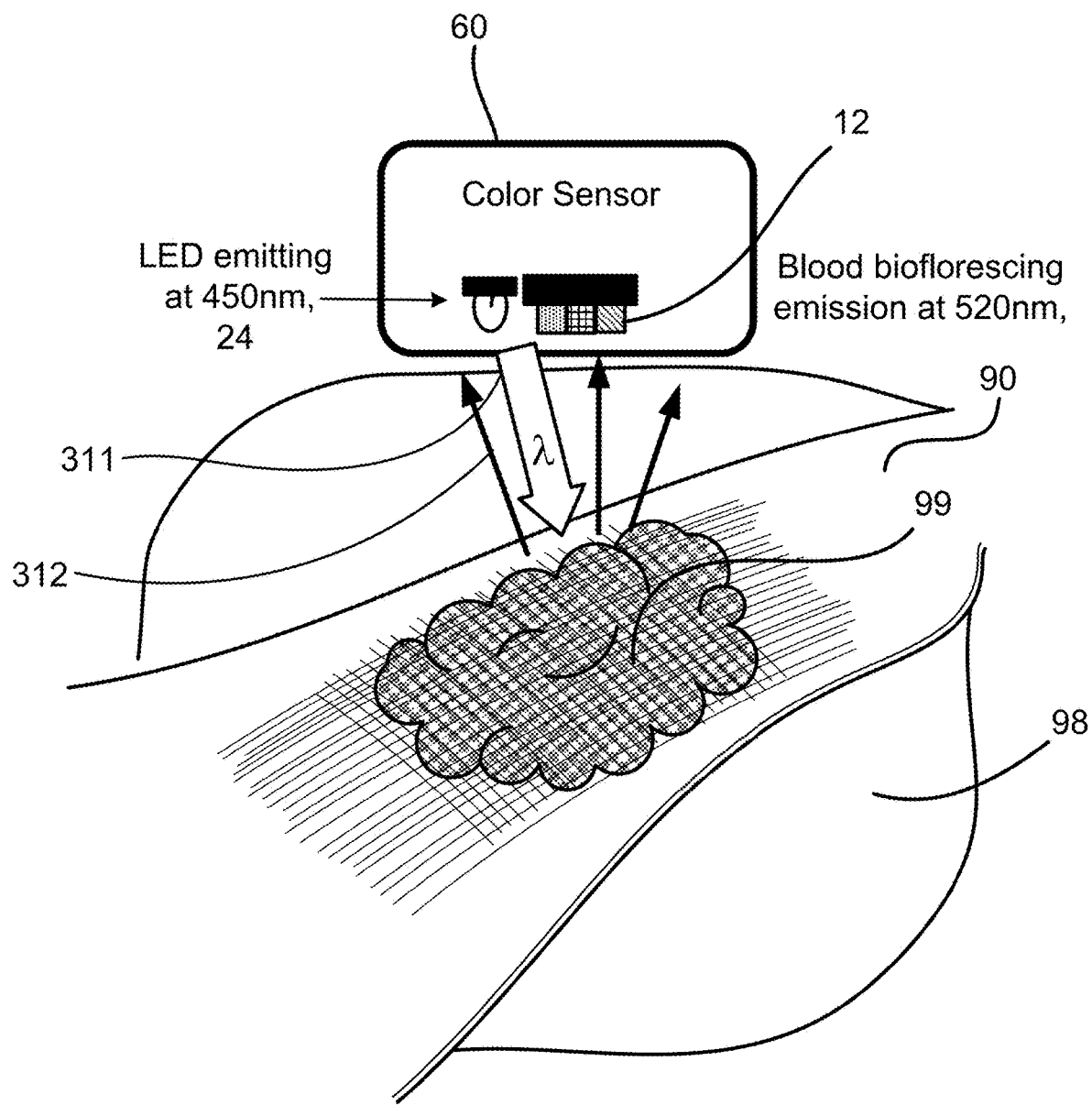

FIGS. 3A and 3B are illustrations of the detections method of a color sensor and illumination device according to the invention. FIG. 3A shows a blood sensor 60 positioned above an absorbent material 90 on a patient 98. The absorbent material contains a blood leak in a sensing region 99 of the blood sensor 60. The illumination device 24 of the blood sensor 60 emits light 301 towards the sensing region 99 and the color sensor 12 receives the scattered or reflected light 302 energy from the blood in the sensing region 99. Based on the properties of the received light energy 302 (e.g., frequency, intensity, or polychromatic ratio) detected by the color sensor 12, the blood sensor 60 is able to determine if the received light energy indicates blood present in the sensing region 99. In FIG. 3B, the illumination device 24 of the blood sensor 60 is emitting light 311 at 450 nm. The emitted light 311 excites a bio-fluorescence in the blood in the sensing region 99, which causes an emission of light energy 312 at 520 nm. In some instances, the color sensor 12 is tuned to detect a very specific wavelength using optical filters or special optical coating to improve signal to noise, or reduce ambient broad band light in the environment. These may be in the form of an optical bandpass filter, or notch filter.

Figure 4:
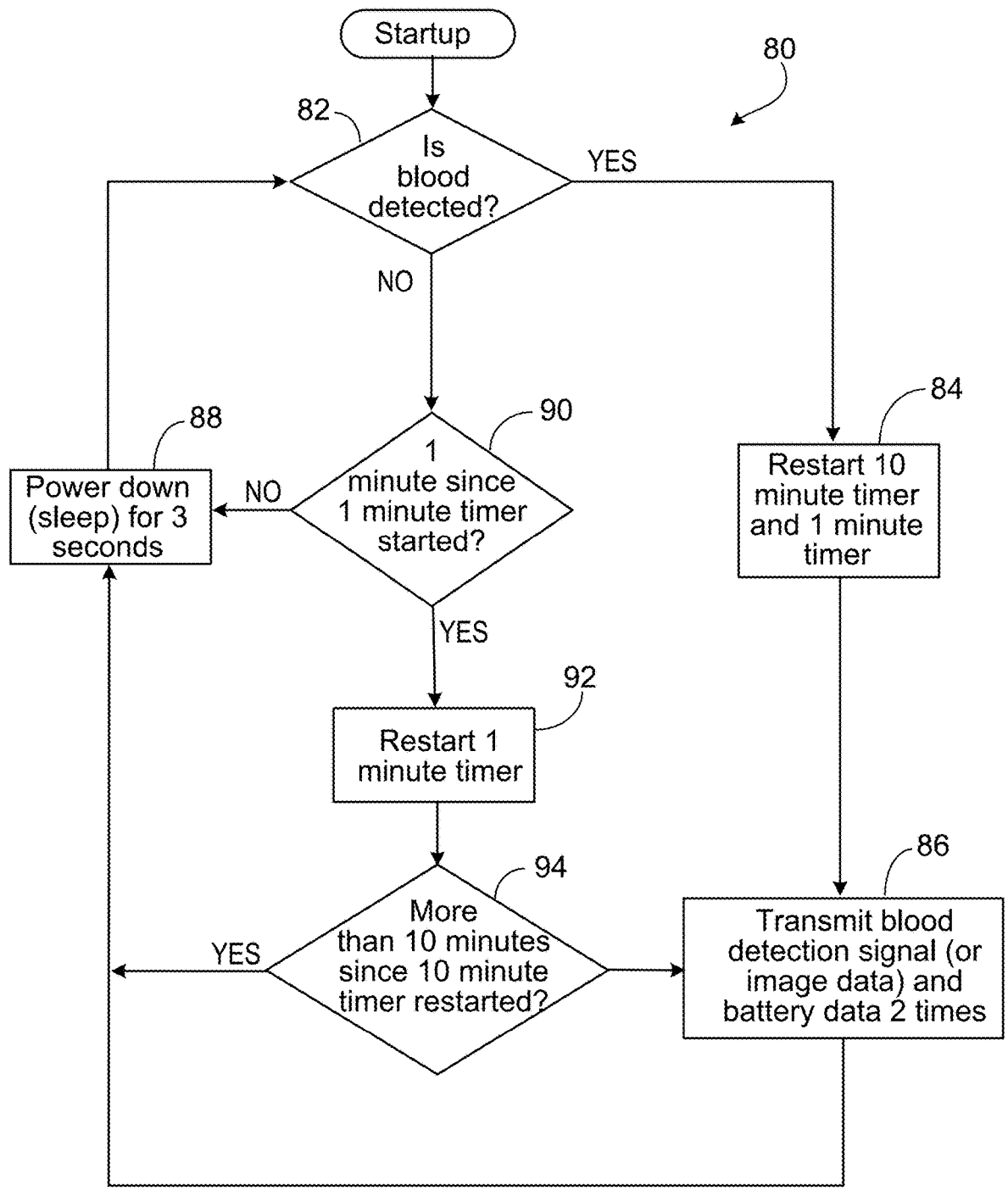
FIG. 4 is a flow diagram illustrating the operation of a blood sensor.

Depicted in FIG. 4 is a flow chart illustrating an example of a process 80 performed by the microcontroller 16 of the blood sensor, including entry of the blood sensor into a low power state, as described previously. The microcontroller 16 determines 82 if a blood detection has been received from the color sensor 12. A blood detection signal would indicate that blood/blood has been detected in the sensing region (i.e., by making a comparison to a blood detection threshold value). If blood has been detected, the microcontroller 16 restarts 84 two timers; one timer set for 10-minutes (10-minute timer) and another set for 1-minute (1-minute timer). When blood has been detected and the 10-minute and 1-minute timers have been reset, the microcontroller 16 transmits 86 a data transmission twice in a row indicating both that blood has been detected and the energy level status of the battery. After transmission of this information the blood sensor 10 powers down 86 (sleeps) for 3 seconds, after which the process 80 returns to decision block 82. If blood is not detected in decision block 82, then the microcontroller 16 determines 90 the status of the 1 minute timer. Thus, if 1 minute has not passed since the 1 minute timer was started then microcontroller 16 directs 90 blood sensor 10 to power down for 3 seconds. Alternatively, if 1 minute has not elapsed since the 1-minute timer was started, then the process 80 proceeds 90 and the 1-minute timer is restarted 92 and then the microcontroller 16 determines 94 if more than 10 minutes have elapsed since the 10-minute timer was restarted. If ten minutes have elapsed since the 10-minute timer was restarted 94, then microcontroller 16 has blood sensor 10 power down 88 for 3 seconds and return to decision block 82. If, instead, more than 10 minutes have not elapsed since the 10-minute timer was restarted, then the microcontroller 16 again transmits a data transmission twice in a row indicating both that blood has been detected and the energy level status of the battery and then directs 88 the blood sensor 10 to enter a low power state for 3 seconds. This process using the two timers allows the blood sensor 10 to continue to send messages for a short amount of time after blood is no longer present, telling the receiver that the blood condition has been cleared and allowing the blood sensor to send a low battery signal even in the event that a blood signal is not also being transmitted. Importantly, the process 80 directs the blood sensor to transmit a blood signal every 3 seconds, ensuring that such a signal would not be missed (e.g., by medical personnel).

Figure 5:
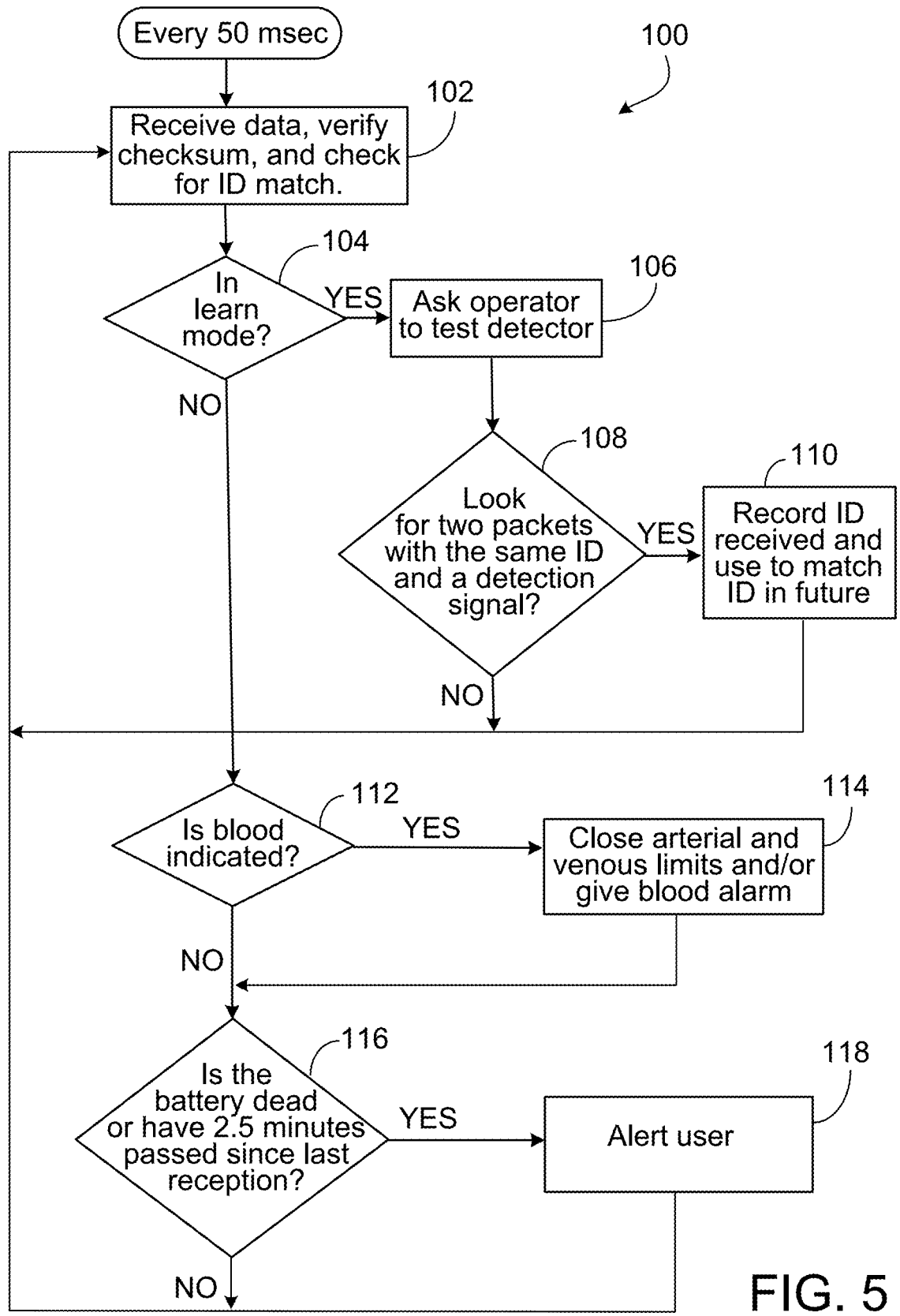
FIG. 5 is a flow diagram illustrating the operation of a receiver unit in response to the detection of a blood leak by a blood sensor.

The operation of a controller in response to detection of a blood leak by a blood sensor during an extracorporeal blood treatment could occur as illustrated in a flow diagram of the process 100 in FIG. 5. In the process 100, every 50 msec receiver unit 40 would receive data transmitted from blood sensor 10 and controller 50 would determine 102 if the identification data (ID) sent by the blood sensor is known. The controller 50 would then determine 104 if the controller 50 in a learning mode and, if so, directs 106 the user/medical personnel (by display of a message on the receiver/system unit) initiate the blood sensor for self-test. The controller 50 then determines 108 if the same blood sensor 10 has sent two signals that blood has been detected (i.e., a blood detection threshold above a specified value) and that the color detected is blood (i.e., a wavelength detected that indicates the presence of blood). Alternatively, if the self-test was not conducted with a sample mimicking blood, any particular sensing surface or light source could be used to initiate the test. In some instances, a specific color is detected by blood sensor to indicate an initiation event. If two blood or initiation signals have been received from the same blood sensor ID, then controller 50 records 110 the ID received to use to match in a future signal transmission. Alternatively, if an initiation signal or a signal of a blood leak has not been received from the same blood sensor ID, the process 100 proceeds back to verify 102 that two signal transmissions of a blood leak or initiation signal have been received from the same blood sensor ID. Based on the information in block 102, the controller 50 then determines 104 if, for the blood sensor ID, it is in learning mode (e.g., the blood sensor ID is known) and, if not, the process 100 proceeds to determine 112 if the blood sensor has detected blood. If the controller 50 determines that blood is indicated by the blood sensor, then the controller triggers 114 one or more alarms and/or stops 114 a blood pump and closes arterial and venous valves. If controller 50 determines 112 that blood is not indicated, the controller 50 ascertains 116 if the blood sensor is functional (e.g., has power or has sent a recent transmission). If the blood sensor 10 is not functional, controller 50 alerts 118 the user. Alternatively, if the blood sensor 10 is functional, the controller 50 would return to the beginning of process 100 upon the next reception 102 of a signal from a blood sensor.

Figure 6B:
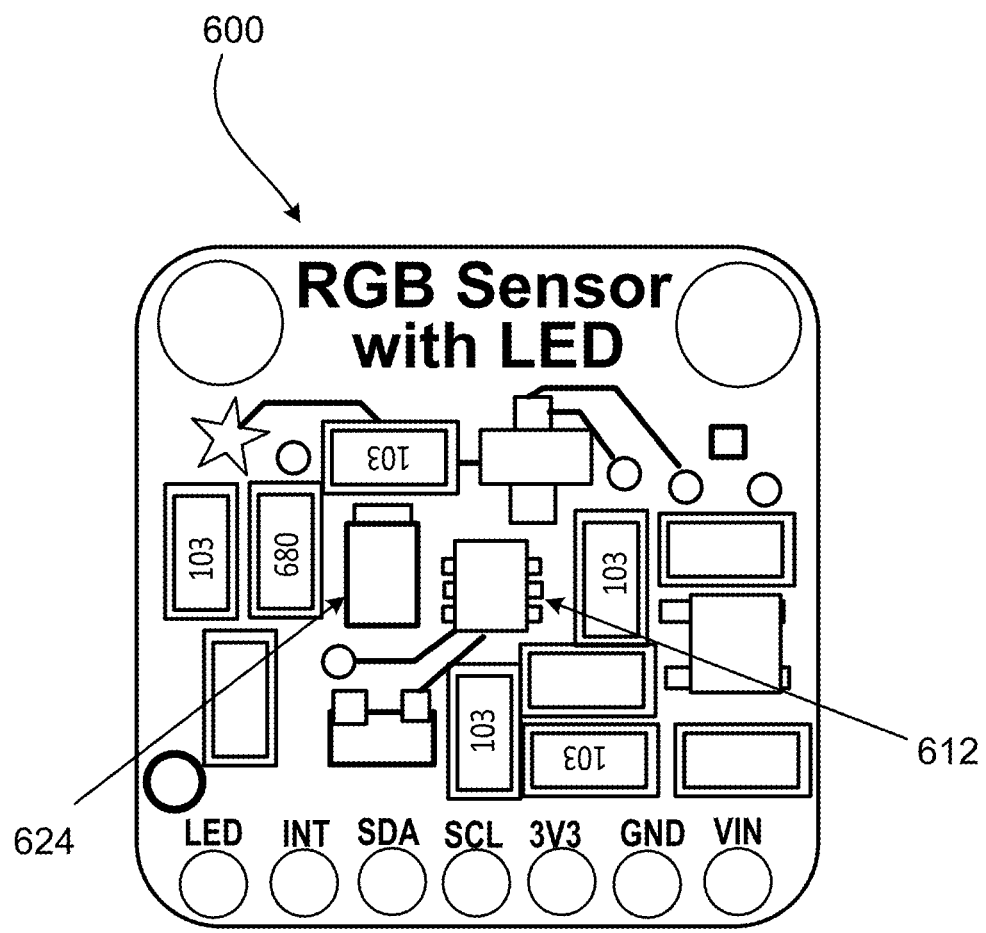

FIGS. 6A and 6B are illustrations of a prototype blood detector system according to the invention and an absorbent material containing blood. FIG. 6A shows a blood sensor 600 including a printed circuit board with an illumination device 624 configured to emit light at 450 nm and a color sensor 612 positioned in close proximity on one end. Adjacent to the blood sensor 600 is an absorbent material 90 with a sensing region 99 saturated with blood. FIG. 6B shows a close-up view of the PCB of the blood sensor 600 including the illumination device 624 and color sensor 612 positioned on the PBC.

Figure 7:
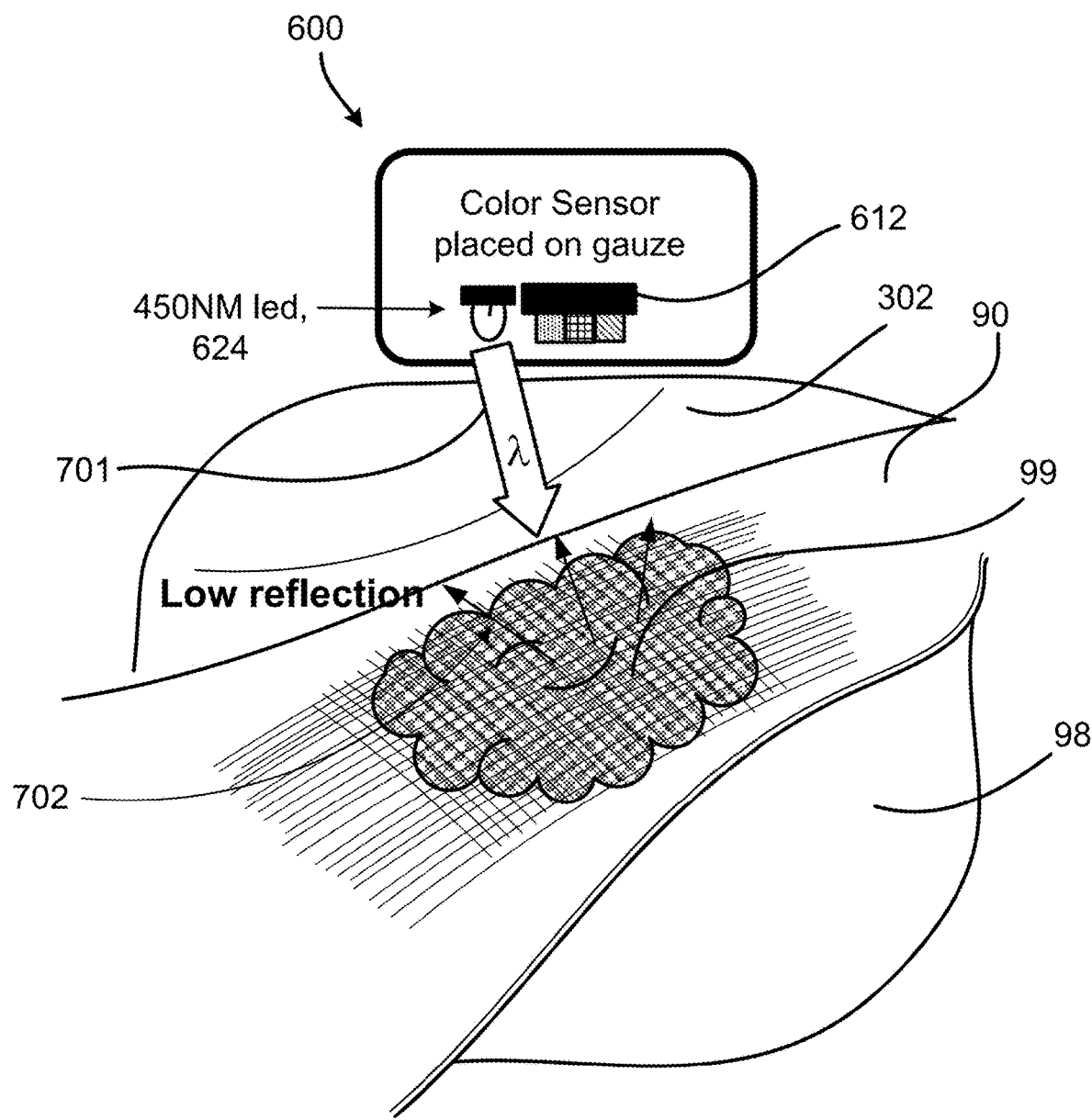
FIG. 7 is an illustration of the operation of a blood detection sensor according to the invention.
Figure 8:
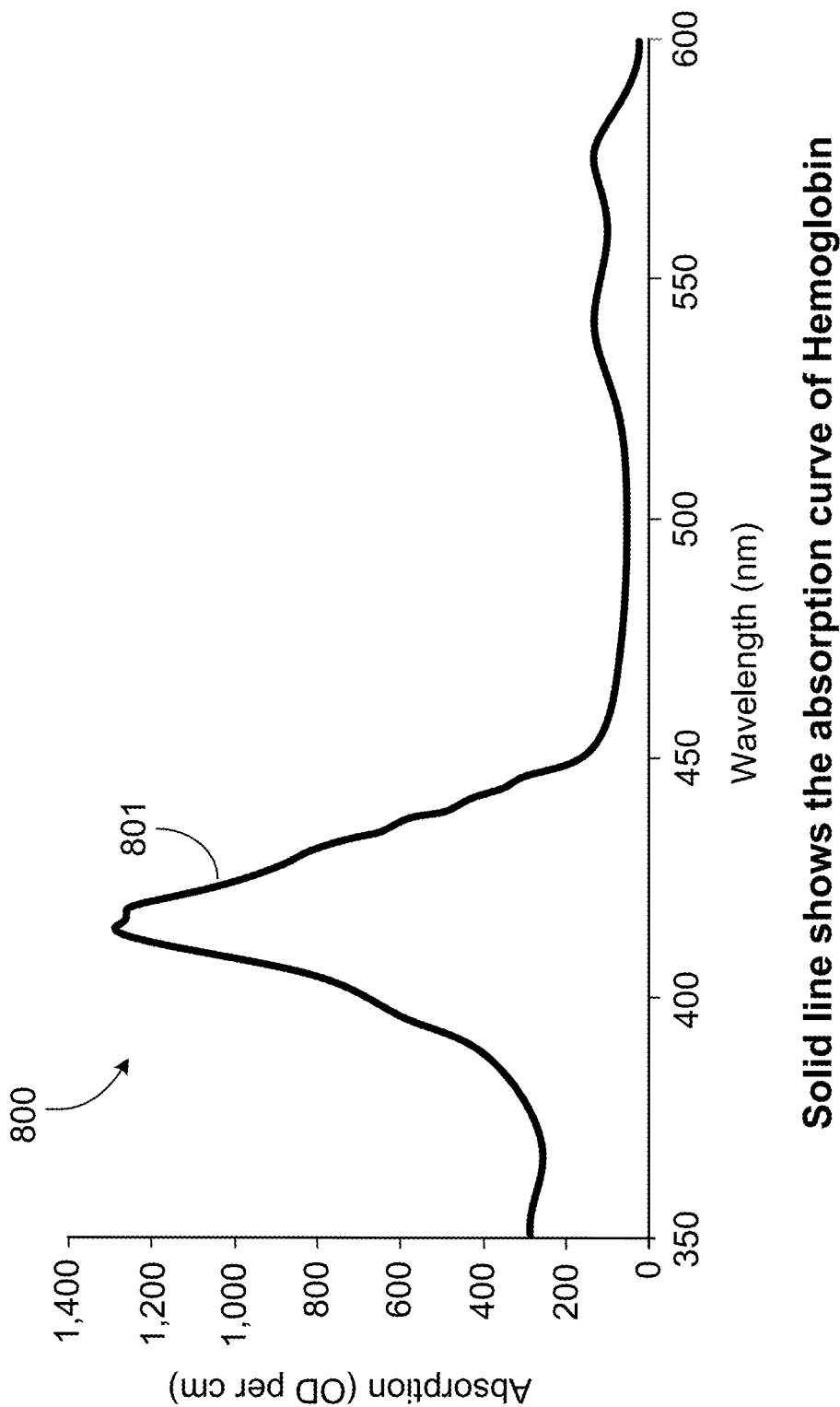
FIG. 8 is a graph of the absorption curve of hemoglobin.

FIG. 7 shows the configuration of a test conducted using the blood sensor 600 placed against the absorbent material 90 while blood was introduced to the sensing region 99. The illumination device 624 emitted light 701 at 450 nm towards the sensing region 99, and the color sensor 612 received the light energy 702 from the sensing region 99 as altered by the presence of blood. Prior to the presence of blood, the color sensor detects reflected light at 450 nm, however the presence of hemoglobin in blood absorbs light as shown in FIG. 8. Accordingly, the presence of blood alters the signal of the light energy received by the color sensor 612 by drastically reducing the intensity of the received light, in agreement with the absorption curve of FIG. 8. FIG. 8 is a graph 800 of the absorption curve 801 of hemoglobin showing the strongest absorption at 450 nm. Therefore, in some instances, the blood detector 600 indicates the presence of blood in the sensing region 99 when the light energy of the blue light (e.g., 450 nm) is decreased by the absorption of the hemoglobin present in the blood and this wavelength causes blood to fluoresce at approximately 520 nm.

Figure 9:
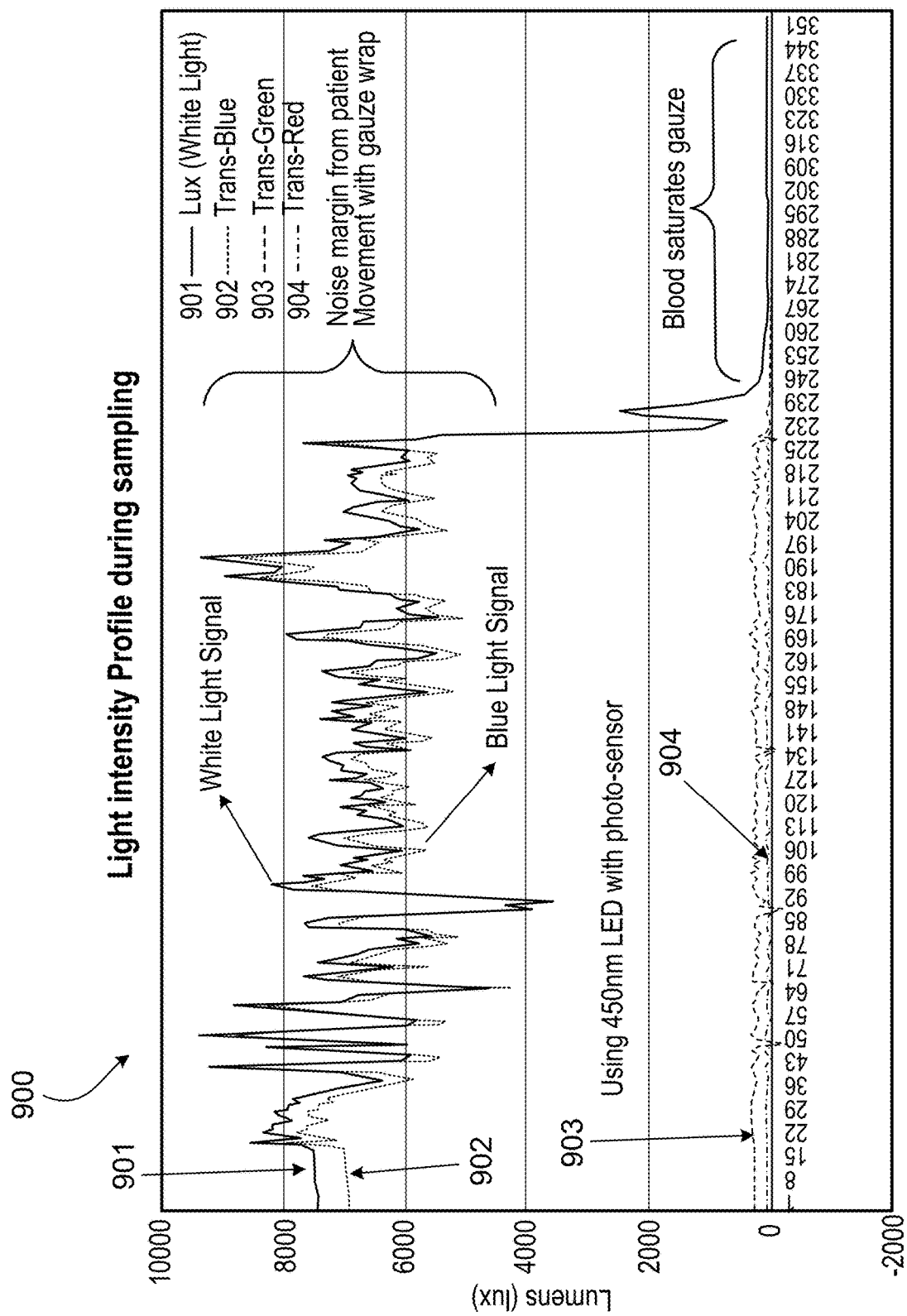
FIG. 9 is a graph of a color sensor's blood detection signal over time.

FIG. 9 is a graph 900 of a color sensor's blood detection signal over time. FIG. 9 shows a graph of light intensity detected by a color sensor over time to simulate a blood leak in a sensing region as illuminated by a white-light LED. Initially, at time 0, the color sensor detects an overall light intensity 901 around 7000 lumens, with the majority color-component of the light being blue light 902 as emitted by the illumination device and reflected from gauze in a sensing region adjacent to the color sensor. In the experimental set-up of FIG. 9, the two signals that best detect the blood are the blue sensor cell (collecting data 902) and the white light sensor cell (collecting data 901). The color sensor collecting the data of FIG. 9 includes 3 red sensor cells, 3 green sensor cells, 3 blue sensor cells, and 3 white sensor cells. Blood is introduced to the gaze (i.e., the sensing region), and the reflected light drops off around the time of 225 (i.e., the blood absorbs the light), and the drop in the reflected light energy indicates the presence of blood in the sensing region interacting with the emitted light.

What is claimed is:

1. A blood detector system for detecting a blood leak at an intravenous injection site, the blood detector system comprising:
a blood sensor comprising:
a support structure comprising (i) a first curved portion comprising one or more clip features configured to attach the blood sensor to a blood line of a medical treatment device and (ii) a second portion defining a recess, the first curved portion extending outward from the second portion and being integrally formed with the second portion,
a light emitting unit located within the recess of the support structure and adapted to emit a white light and illuminate a sensing region adjacent to the blood sensor with the white light;
a planar transparent cover (i) positioned over a side of the second portion of the support structure to offset the side of the support structure from the sensing region, and (ii) sized such that the entire planar transparent cover is positioned within an outer profile of the second portion of the support structure;
a color sensor attached to the support structure and located within the recess of the support structure such that the planar transparent cover is located between the sensing region and the color sensor during use of the blood detector system for detecting the blood leak, the color sensor adapted to detect light from the sensing region adjacent to the color sensor, and the color sensor being configured to detect (i) reflected light of a wavelength associated with blood and (ii) emitted light associated with bio-fluorescence of blood, the color sensor comprising a color image sensor and a lens arranged to project an image of the sensing region onto a plurality of pixels of the color image sensor to detect blood in the projected image of the sensing region;
an electronic transmitter attached to the support structure,
an antenna coupled to the electronic transmitter,
a power source connected to the electronic transmitter, the light emitting unit, and the color sensor,
wherein the blood detector system is configured to detect blood by
measuring an intensity of white light reflected or emitted by a fluid of the sensing region when the sensing region is illuminated with the white light;
measuring an intensity of blue light reflected or emitted by the fluid of the sensing region when the sensing region is illuminated with the white light; and
determining that the fluid is blood by determining whether the measured intensity of white light is below a first threshold and whether the measured intensity of blue light is below a second threshold such that the fluid is determined to be blood when the measured intensity of white light is below the first threshold and the measured intensity of blue light is below the second threshold,
wherein the blood detector system is configured to, in response to determining that the fluid is blood, control the light emitting unit to emit a light of a different wavelength than the emitted white light to confirm that the fluid is blood, wherein the blood sensor is configured to enter an activated state from a low-power state when the measured intensity of white light is below the first threshold, a receiver for receiving one or more signals from the blood sensor, a controller in communication with the receiver, and an alert system in communication with the controller.

2. The blood detector system of claim 1, wherein the second portion of the support structure comprises an opaque region sized and positioned to occlude ambient light from directly reaching the sensing region.

3. The blood detector system of claim 1, further comprising a processor disposed in the support structure and in communication with the electronic transmitter and the color sensor, the processor being configured to determine that the fluid is blood based on the image of the sensing region projected by the lens and detected by the color image sensor by determining whether the measured intensity of white light as detected by the color image sensor is below the first threshold and whether the measured intensity of blue light as detected by the color image sensor is below the second threshold.

4. The blood detector system of claim 3, wherein the processor is configured to direct the electronic transmitter to transmit, to the receiver, at least one signal indicating that blood has been detected.

5. The blood detector system of claim 1, wherein the controller is configured to determine that the fluid is blood based on one or more signal transmissions from the blood sensor by determining whether the measured intensity of white light represented in the one or more signal transmissions is below the first threshold and whether the measured intensity of blue light represented in the one or more signal transmissions is below the second threshold.

6. The blood detector system of claim 1, wherein the power source comprises a rechargeable energy storage module or a replacement energy storage module.

7. The blood detector system of claim 1, wherein the sensing region comprises an absorbent material and the blood detector system is configured to determine that fluid on the absorbent material is blood.

8. The blood detector system of claim 1, wherein the one or more clip features are adapted to position the color sensor above an entry point of an intravenous needle of the blood line while the blood line is received in the first curved portion of the support structure and the blood line is attached to the medical treatment device.

9. The blood detector system of claim 1, wherein the planar transparent cover is positioned in an optical path of the color sensor such that light propagates from the light emitting unit through the planar transparent cover to the sensing region, and light propagates from the fluid of the sensing region through the planar transparent cover and the lens to the color sensor.

10. The blood detector system of claim 1, wherein the light emitting unit comprises a white light emitting diode configured to emit the white light.

11. The blood detector system of claim 1, wherein the color sensor comprises one or more infrared sensors.

12. The blood detector system of claim 1, wherein the color sensor is adapted to detect light having a wavelength of at least one of 274 nm, 345 nm, 415 nm, 541 nm, and 576 nm.

13. The blood detector system of claim 1, wherein the controller is configured to trigger the alert system in response to the controller receiving one or more signals from the receiver, the alert system comprising one or more alarms selected from the group consisting of a display of a warning message, an audible alarm, a visual alarm, and a physical alert.

14. The blood detector system of claim 1, wherein the color sensor comprises red, blue, and green color sensing regions, and the blood detector system is configured to determine that the fluid is blood based on the blue sensing region.

15. The blood detector system of claim 1, wherein the blood sensor comprises a printed circuit board, and the color sensor and the light emitting unit are disposed on the printed circuit board.

16. The blood detector system of claim 1, wherein the light emitting unit is a light emitting diode (LED).

17. A blood detector for detecting a blood leak at an intravenous injection site, the blood detector comprising:

a support structure comprising (i) a first curved portion comprising one or more clip features configured to attach the blood detector to a blood line of a medical treatment device and (ii) a second portion defining a recess, the first curved portion extending outward from the second portion and being integrally formed with the second portion;

a light emitting unit located within the recess of the support structure and adapted to emit a white light and illuminate a sensing region adjacent to the blood detector with the white light;

a planar transparent cover (i) positioned over a side of the second portion of the support structure to offset the side of the support structure from the sensing region, and (ii) sized such that the entire planar transparent cover is positioned within an outer profile of the second portion of the support structure;

a color sensor adapted to detect light from the sensing region, the color sensor located within the recess of the support structure such that the planar transparent cover is located between the sensing region and the color sensor during use of the blood detector for detecting the blood leak, the color sensor comprising a color image sensor and a lens arranged to project an image of the sensing region onto a plurality of pixels of the color image sensor to detect blood in the projected image of the sensing region;

an electronic transmitter;

an antenna coupled to the electronic transmitter; and a power source connected to the electronic transmitter, light emitting unit, and color sensor, wherein the blood detector is configured to detect blood by measuring an intensity of white light reflected or emitted by a fluid of the sensing region when the sensing region is illuminated with the white light;

measuring an intensity of blue light reflected or emitted by the fluid of the sensing region when the sensing region is illuminated with the white light; and determining that the fluid is blood by determining whether the measured intensity of white light is below a first threshold and whether the measured intensity of blue light is below a second threshold such that the fluid is determined to be blood when the measured intensity of white light is below the first threshold and the measured intensity of blue light is below the second threshold, wherein the blood detector is configured to (i) enter an activated state from a low-power state when the measured intensity of white light is below the first threshold and (ii) in response to determining that the fluid is blood, control the light emitting unit to emit a light of a different wavelength than the emitted white light to confirm that the fluid is blood.

18. A method of detecting a blood leak at an intravenous injection site comprising:
attaching a blood sensor to an absorbent material surrounding a needle insertion site, the blood sensor comprising:
a support structure comprising (i) a first curved portion comprising one or more clip features configured to attach the blood sensor to a blood line of a medical treatment device and (ii) a second portion defining a recess, the first curved portion extending outward from the second portion and being integrally formed with the second portion,
a light emitting unit attached to the support structure and located within the recess of the support structure and, the light emitting unit adapted to emit a white light and illuminate a sensing region of the absorbent material with the white light,
a planar transparent cover (i) positioned over a side of the support structure to offset the side of the second portion of the support structure from the sensing region, and (ii) sized such that the entire planar transparent cover is positioned within an outer profile of the support structure,
a color sensor attached to the support structure, the color sensor adapted to receive light reflected from the sensing region of the absorbent material, the color sensor located within the recess of the support structure such that the planar transparent cover is located between the sensing region and the color sensor during use of the blood sensor for detecting the blood leak,
an electronic transmitter attached to the support structure,
an antenna coupled to the electronic transmitter,
a microcontroller in communication with the electronic transmitter and the color sensor, the microcontroller being configured to detect a presence of blood in the sensing region based on a color of the reflected light, and
a power source connected to the microcontroller, electronic transmitter, light emitting unit, and color sensor,
wherein the blood sensor is configured to detect blood by
measuring an intensity of white light reflected or emitted by a fluid of the sensing region when the sensing region is illuminated with the white light;
measuring an intensity of blue light reflected or emitted by the fluid of the sensing region when the sensing region is illuminated with the white light; and
determining that the fluid is blood by determining whether the measured intensity of white light is below a first threshold and whether the measured intensity of blue light is below a second threshold such that the fluid is determined to be blood when the measured intensity of white light is below the first threshold and the measured intensity of blue light is below the second threshold,
wherein the blood sensor is configured to (i) direct the electronic transmitter to transmit, to a receiver unit in communication with the blood sensor, at least one signal that blood has been detected, whereby the receiver unit triggers an alert system and (ii) in response to determining that the fluid is blood, control the light emitting unit to emit a light of a different wavelength than the emitted white light to confirm that the fluid is blood.

19. The blood detector system of claim 1, wherein the planar transparent cover is sized and arranged to position the color sensor and the light emitting unit the same distance away from the sensing region.

20. The blood detector system of claim 1, wherein the blood sensor is configured to enter the low-power state for a predetermined period of time when the measured intensity of white light is above the first threshold.

21. The blood detector system of claim 1, wherein the emitted white light has a wavelength between 400 and 700 mm and the blue light reflected or emitted by the fluid of the sensing region has a wavelength of 450 nm.

22. The blood detector system of claim 1, wherein the color sensor is configured to measure a 7000 lumen intensity of white light and a 7000 lumen intensity of blue light.

23. The blood detector system of claim 1, wherein the color sensor is configured to measure an intensity of green light and an intensity of red light, and the blood detector system is configured to detect blood irrespective of the measured intensity of the green light and the measured intensity of the red light.

24. The blood detector system of claim 1, wherein the first curved portion of the support structure is positioned on a single side of the second portion of the support structure.

25. The blood detector system of claim 24, wherein the first curved portion of the support structure comprises a semi-circular opening for receiving the blood line.

26. The blood detector system of claim 25, wherein a longitudinal axis of the semi-circular opening is substantially perpendicular to an optical path between the color sensor and the sensing region, the optical path substantially perpendicular to a planar surface of the planar transparent cover and passing through the planar transparent cover.

27. The blood detector system of claim 1, wherein the color sensor is configured to detect a color, a size, and a location of the fluid of the sensing region based on the projected image.

* * * * *

UNITED STATES PATENT AND TRADEMARK OFFICE
CERTIFICATE OF CORRECTION

PATENT NO. : 11,826,545 B2
APPLICATION NO. : 15/259754
DATED : November 28, 2023
INVENTOR(S) : Philip Scott James It is certified that error appears in the above-identified patent and that said Letters Patent is hereby corrected as shown below:

In the Claims

Column 22, Line 26, in Claim 21, delete "mm" and insert --nm--.

Signed and Sealed this
Thirtieth Day of January, 2024

*Katherine Kelly Vidal*

Katherine Kelly Vidal
*Director of the United States Patent and Trademark Office*